(12) United States Patent
Döring et al.

(10) Patent No.: US 7,858,775 B2
(45) Date of Patent: Dec. 28, 2010

(54) PRODUCTION OF 2'-DEOXYNUCLEOSIDES AND 2'-DEOXYNUCLEOSIDE PRECURSORS FROM 2-DEHYDRO-3-DEOXY-D-GLUCONATE

(75) Inventors: Volker Döring, Paris (FR); Denis Thibaut, Paris (FR); Annett Kreimeyer, Combs la Ville (FR); Philippe Marliere, 5 rue Gossec, Paris (FR) F-75012

(73) Assignees: Rhodia Chimie, Aubervilliers (FR); Evologic S.A., Marliere Technologies Societe Civile, Evry (FR); Philippe Marliere, Paris (FR)

( * ) Notice: Subject to any disclaimer, the term of this patent is extended or adjusted under 35 U.S.C. 154(b) by 890 days.

(21) Appl. No.: 10/560,760

(22) PCT Filed: Jun. 24, 2004

(86) PCT No.: PCT/EP2004/006848
§ 371 (c)(1),
(2), (4) Date: Oct. 6, 2006

(87) PCT Pub. No.: WO2004/113358

PCT Pub. Date: Dec. 29, 2004

(65) Prior Publication Data

US 2007/0212759 A1   Sep. 13, 2007

(30) Foreign Application Priority Data

Jun. 24, 2003 (EP) .................................. 03013457

(51) Int. Cl.
*C07H 1/00* (2006.01)
*C07H 3/02* (2006.01)
*C07H 3/08* (2006.01)
*C12N 9/00* (2006.01)

(52) U.S. Cl. ........................ 536/124; 536/22.1; 435/183
(58) Field of Classification Search ................. 536/124, 536/22.1; 435/183
See application file for complete search history.

(56) References Cited

U.S. PATENT DOCUMENTS 5,759,825 A * 6/1998 Wong .......................... 435/136
5,872,247 A * 2/1999 Fleche et al. ................. 536/124

OTHER PUBLICATIONS

De Ley, J. Naturwissenschaften, 1955, 42(4), p. 96.*
Candy et al. Biochimica et Biophysica Acta, 1998, 1385, p. 323-338.*
CRC Handbook of Chemistry and Physics, Handbook of Chemistry & Physics Online, www.hbcpnetbase.com, accessed online on May 4, 2009.*

* cited by examiner

*Primary Examiner*—Shaojia Anna Jiang
*Assistant Examiner*—Jonathan S Lau
(74) *Attorney, Agent, or Firm*—Buchanan Ingersoll & Rooney PC

(57) ABSTRACT

This invention relates to a process for preparing 2'-deoxynucleoside compounds or 2'-deoxynucleoside precursors using 2-dehydro-3-deoxy-D-gluconic acid (usually abbreviated as KDG) or its salts as a starting material. A variety of 2'-deoxynucleosides and their analogues are used as a starting material for synthesis or drug formulation in production of an antiviral, anticancer or antisense agent.

21 Claims, No Drawings

PRODUCTION OF 2'-DEOXYNUCLEOSIDES AND 2'-DEOXYNUCLEOSIDE PRECURSORS FROM 2-DEHYDRO-3-DEOXY-D-GLUCONATE

This application is an application under 35 U.S.C. Section 371 of International Application Number PCT/EP2004/006848 filed on Jun. 24, 2004.

This invention relates to a process for preparing 2'-deoxynucleoside compounds or 2'-deoxynucleoside precursors using 2-dehydro-3-deoxy-D-gluconic acid (usually abbreviated as KDG) or its salts as a starting material. A variety of 2'-deoxynucleosides and their analogues are used as a starting material for synthesis or drug formulation in production of an antiviral, anticancer or antisense agent.

Specifically, the invention relates to a method in which KDG or a derivative of KDG is subjected to a decarboxylation step to remove the original carboxy group of KDG. In a preferred embodiment, the KDG used in the method according to the invention is enzymatically produced from D-gluconate or D-glucosaminate.

2'-deoxynucleosides and 2'-deoxynucleoside precursors including 2-deoxy-D-ribose are used as starting material for synthesis or drug formulation, for instance, in production of antiviral and anticancer agent. 2'-deoxynucleosides or derivatives thereof and 2'-deoxynucleoside precursors are also used as reagents for research, diagnosis and synthesis of therapeutic antisense molecules.

In one method of the prior art, deoxynucleosides are generated from biological materials such as testis (WO 99/49074) or yeast or fish sperm by enzymatic cleavage of DNA. This method, however, involves several disadvantages, in particular regarding difficulties of obtaining the starting material in sufficient quantity and quality.

The main production process of 2-deoxy-D-ribose currently consists in chemical hydrolysis of DNA. In this case, the deoxyribosyl moiety originates in ribonucleotide reductase activity. No synthesis of 2-deoxy-D-ribose from KDG has been yet described.

In most living cells, deoxyribonucleosides result from a "salvage pathway" of the nucleotide metabolism. The deoxyribose moiety of deoxyribonucleosides is obtained through the reduction of a ribosyl moiety into di- or triphosphate ribonucleotides catalyzed by ribonucleotide reductases. However, the deoxyribose moiety is not recycled, but is degraded into D-glyceraldehyde-3-phosphate and acetaldehyde following the reactions of central metabolism:

deoxynucleoside is cleaved into deoxyribose-1-phosphate and nucleobase through phosphorolysis mediated by products of the genes encoding thymidine phosphorylase (deoA), purine-nucleoside phosphorylase (deoD), uridine phosphorylase (udp) or xanthosine phosphorylase (xapA).

deoxyribose-1-phosphate is converted into deoxyribose-5-phosphate through a reaction catalyzed by deoxyribose phosphate mutase (deoB), which is further degraded to D-glyceraldehyde-3-phosphate and acetaldehyde through a reaction catalyzed by deoxyribose-5-phosphate aldolase (deoC).

It has been shown that the deo enzymes also catalyze in vitro the reverse anabolic reactions: Deoxyribose-5-phosphate is obtained in vitro in the presence of purified *Escherichia coli* or *Lactobacillus plantarum* deoxyribose aldolase starting from acetaldehyde and D-glyceraldehyde-3-phosphate (Rosen et al., J. Biol. Chem., 240, (1964), 1517-1524; Pricer, J. Biol. Chem., 235, (1960), 1292-1298). Deoxyribose can also be obtained with acetaldehyde and glyceraldehyde as enzyme substrates, but only with a very low yield (Barbas, J. Am. Chem. Soc. 112 (1990), 2013-2014).

The patent application WO 01/14566 describes the enzymatic synthesis of deoxynucleosides starting from deoxyribose-1-phosphate through the combined activities of three enzymes of the deo operon, i.e. deoxyribose aldolase, deoxyribomutase and phosphorylase (thymidine or purine nucleoside phosphorylase) in a one-pot reaction, using as starting substrates glyceraldehyde-3-phosphate, acetaldehyde and a nucleobase. D-glyceraldehyde-3-phosphate can be obtained from fructose-1,6-bisphosphate by an enzymatic process.

The patent application EP 1179598 describes the use of phosphorylase to catalyze the enzymatic production of deoxynucleosides starting from deoxyribose-1-phosphate and nucleobase. The yield of deoxynucleoside synthesis is improved by precipitation of phosphate.

However, methods using enzymes of the deo operon working in the reverse direction compared to their biological function show low yields, which indicates serious drawbacks for their use.

In view of the above-described ineffectiveness of the currently applied processes for producing deoxynucleosides and deoxynucleoside precursors, it is an object of the present invention to provide means and methods for the biosynthetic production of deoxynucleosides and deoxynucleoside precursors starting from cheap and commercially available compounds without being dependent on unreliable natural sources.

In particular, there is a need for alternative methods for the production of deoxynucleosides and deoxynucleoside precursors which allow efficient and economical synthesis of deoxyribonucleosides, by means of which the drawbacks of prior art processes are eliminated.

The present invention relates to a method for producing 2'-deoxynucleosides and precursors thereof starting from 2-dehydro-3-deoxy-D-gluconic acid (KDG) or its salts and comprising a decarboxylation step.

In particular, this method is useful for producing 2-deoxy-D-ribose (DRI) as well as synthetically versatile enamine derivatives of DRI as 2'-deoxynucleoside precursors.

The decarboxylation step takes place by reacting either KDG or its salts directly, or a derivative of KDG, usually to cleave the C1-C2 bond of the KDG.

In one embodiment of the invention, KDG or one of its salts undergoes (oxidative) decarboxylation leading to 2-deoxy-D-ribonic acid (DRN) or its salts, itself being further converted into 2-deoxy-D-ribose (DRI) or 2-deoxy-D-ribitol (DRL).

In another embodiment of the invention, decarboxylation takes place by reacting KDG or its salts with an amine, leading to an enamine derivative. This high energy enamine derivative can be further converted into DRI by hydrolysis.

In another embodiment of the invention, (oxidative) decarboxylation is carried out on 3-deoxy-D-gluconic acid (DGN) or its salts and/or 3-deoxy-D-mannonic acid (DMN) or its salts as derivatives of KDG, leading to DRI. Production of a mixture of DGN and DMN takes place by reduction of KDG. The decarboxylation is preferably carried out via reaction with hydrogen peroxide.

In another embodiment of the invention, (oxidative) decarboxylation is carried out on 3-deoxy-D-glucosaminic acid (DGM) or its salts and/or 3-deoxy-D-mannosaminic acid (DMM) or its salts, leading to DRI. Production of a mixture of DGM and DMM takes place from KDG by reductive amination.

Another aspect of the invention is a convenient and cost-effective method for preparing KDG or its salts to be used in the above methods. This method starts either from D-gluconate or from D-glucosaminate through the use of recombinant enzymes. The invention provides a novel nucleotide sequence encoding a polypeptide having D-gluconate dehydratase activity and a nucleotide sequence encoding a polypeptide having D-glucosaminate deaminase activity.

The starting material used for the method of the present invention is KDG, represented by formula (I) below or one of its salts, or a protected derivative thereof wherein one or more of the hydroxyl groups at positions 4, 5 and/or 6 are protected by a protection group known in the art.

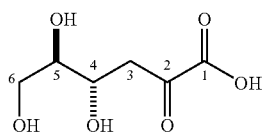
(I)

The term "2'-deoxynucleoside" as used herein relates to 2'-deoxyribonucleosides which are N-glycosides, and wherein the basic N-atom of the nucleobase or nucleobase analog is bound to the anomeric carbon atom of 2-deoxy-D-ribose, or one of its derivatives. Examples of a suitable nucleobase are adenine, cytosine, guanine, thymine, uracil, 2,6-diaminopurine, and hypoxanthine. Examples of nucleobase analogs are 5-azacytosine, 2-chloro-adenine, 5-iodo-cytosine, 8-aza-guanine, 5-iodo-uracil, 5-bromo-uracil, 5-fluoro-uracil, 5-ethyl-uracil and 5-trifluoromethyl-uracil.

The term "2'-deoxynucleoside precursors" as used herein, relates to compounds which can be easily converted into 2'-deoxynucleosides by applying methods known in the prior art. Preferred 2'-deoxynucleoside precursors are 2-deoxy-D-ribose (DRI) or carbohydrate compounds which can be converted into the 2-deoxy-D-ribosyl moiety of 2'-deoxynucleosides, for instance, those established in the prior art 1-phospho-2-deoxy-D-ribose, 5-phospho-2-deoxy-D-ribose and those established by the present invention 2-deoxy-D-ribitol, 2-deoxy-D-ribonic acid, 2-deoxy-D-ribono-1,4-lactone, 1-N-morpholino-3,4,5-trihydroxy-pentene-1, and their derivatives.

The method of the invention encompasses methods wherein the decarboxylation step is directly carried out on KDG or its salts or on compounds derived from KDG. Preferred KDG derivatives are 3-deoxy-D-gluconic acid, 3-deoxy-D-mannonic acid, 3-deoxy-D-glucosaminic acid and 3-deoxy-D-mannosaminic acid and their respective salts.

Furthermore, KDG and its salts or protected forms of these wherein one or more of the hydroxyl groups at the positions 4, 5 and/or 6 are replaced by protecting groups known for that purpose in the art are also suitable starting materials for the decarboxylation reaction of the present invention. Unless noted otherwise, any reference to KDG in the following specification embraces protected forms of KDG, just as reference to KDG derivatives is intended to embrace protected forms of these derivatives. Similarly, any reference to the products obtained in the methods of the invention is intended to encompass protected forms of these products. Preferred protection groups for the purpose of the invention are those which replace the respective hydroxyl groups by acetate ester, benzoate ester, allyl ether, benzyl ether, trityl ether, ter-butyldimethylsilyl (TBDMS) ether, isopropylidene or a benzylidene acetal.

It should be understood that, depending on suitable reaction conditions for the embodiments of the invention, the carboxylic groups contained in the organic acids used as reactants or obtained as products can be in a protonated form or in their salt form, or may be present in equilibrium. Exemplary salts of these acids are those which have metal or ammonium ions as counterions, particularly alkali metal ions such as sodium and/or potassium.

Most of the carbohydrate compounds and their derivatives described in the present invention exist under several cyclic form but for simplicity reasons have been represented by open chain formulas. It is understood that the present invention encompasses all these isomeric or tautomeric forms.

In a first embodiment of the invention, KDG or its salts is reacted with hydrogen peroxide and undergoes (oxidative) decarboxylation to 2-deoxy-D-ribonic acid (DRN), a compound of formula (II) or its salts.

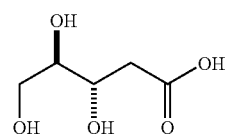
(II)

The product may be further converted into or 2-deoxy-D-ribitol (DRL), represented by formula (IV)

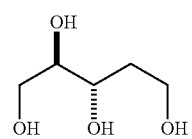
(IV)

or 2-deoxy-D-ribose (DRI), represented by formula (III)

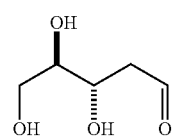
(III)

DRN, DRL and particularly DRI are among preferred 2'-deoxynucleoside precursors for the purpose of the present invention. Conversion of DRN to DRI may proceed directly or via DRL as an intermediate.

Preferably, the preparation of DRN is carried out by oxidative decarboxylation of sodium or potassium 2-dehydro-3-deoxy-D-gluconate in aqueous solution with hydrogen peroxide at room temperature as described in example 5. A general method for the preparation of aldonic acids by oxidative decarboxylation of 2-ketoaldonic acids is described in patent EP 1 038 860 A1.

Preferably, the preparation of DRL is carried out by hydrogenation of 2-deoxy-D-ribonolactone in aqueous solution with Rhodium catalyst on carbon at a temperature of 130° C. under a pressure of 80 bars as described in example 6. 2-Deoxy-D-ribonolactone can be easily prepared by converting a 2-deoxy-D-ribonate (DRN salt) into 2-deoxy-D-ribonic acid, which is in equilibrium with its lactonic form in aqueous solutions (Han, Tetrahedron. 1993. 49, 349-362; Han, Tetrahedron Asymmetry. 1994. 5, 2535-62).

Preferably the preparation of 2-deoxy-D-ribose (DRI) is carried out by oxidization of 2-deoxy-D-ribitol (DLR), e.g. with chromium oxide in pyridine.

In another embodiment of the invention, decarboxylation takes place by reacting (KDG) or its salts with an amino group-containing reagent Y—H leading to a compound of formula (V).

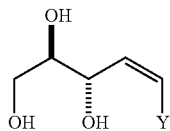

(V)

or its respective trans isomer or a protected form thereof, as a 2'-deoxynucleoside precursor. Y—H represents an amine with the hydrogen atom H bound to the nitrogen of the amino group.

In a preferred embodiment of the invention, the amino group-containing reagent represented by Y—H is a linear or cyclic secondary amine; a primary amine that possess a β-carbonyl group, preferably 3-amino-2-indolinone which was found to be effective for the decarboxylation of α-keto acids (Hanson, J. Chem. Education, 1987, 591-595). In each of these cases, —Y in formula (V) represents the respective nitrogen containing residue derived from these amino-group containing reagent.

Preferably, the compound of formula (V) represents an enamine produced via reaction of a linear or cyclic secondary amine as Y—H.

Preferred cyclic secondary amines are morpholine, pyrrolidine, piperidine, or N-methyl piperazine; preferred non-cyclic amines are those of the formula $R_1$—NH—$R_2$, wherein $R_1$ and $R_2$ independently represent a linear or branched alkyl group of 1-8, preferably 1 to 4 carbon atoms. Particularly preferred as a non-cyclic amine is diethylamine.

Particularly preferred as a cyclic amine is morpholine.

The compound of formula (V) or its trans isomer or a protected form thereof can be further reacted with Z—H, wherein H represents a hydrogen atom and Z represents a leaving group, to produce a compound of formula (VI)

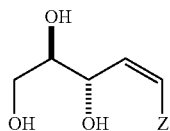

(VI)

or its respective trans isomer or a protected form thereof, as a 2'-deoxynucleoside precursor. Z—H is preferably water, in which case the compound of formula (VI) is DRI or a protected form thereof (keto-enol-tautomerism).

Preferably, the preparation of the compound of formula (V) is carried out by reacting KDG in benzene with the amine, e.g. morpholine under reflux using the method described in example 7, leading to 1-N-morpholino-3,4,5-trihydroxy-pentene-1. Acid catalysed hydrolysis with water yields 2-deoxy-D-ribose (DRI)

A general route to aldehydes via enamines from α-oxocarboxylic acids carrying β-hydrogens is described by Stamos (Tetrahedron Lett. 23 (1982), 459462). Other methods for the preparation and hydrolysis of enamines have been described elsewhere (Stork, J. Am. Chem. Soc. 85 (1963), 207-222; Stamhuis, J. Org. Chem. 30 (1965), 2156-2160).

In another embodiment of the invention, KDG or its salt is converted to 3-deoxy-D-gluconic acid (DGN) and/or 3-deoxy-D-mannonic acid (DMN) represented by formula (VII) or the salts of these compounds

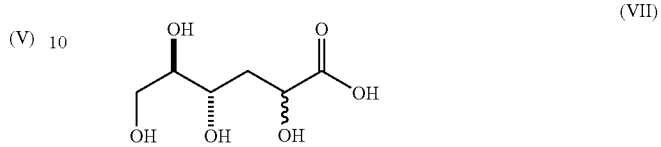

(VII)

The products resulting from this reaction undergo (oxidative) decarboxylation, preferably using hydrogen peroxide, to yield DRI. Production of a mixture of DGN and DMN or their salts takes place from KDG or its salts by reduction.

Preferably the preparation of 2-deoxy-D-ribose (DRI) is carried out by non-stereoselective reduction of 2-dehydro-3-deoxy-D-gluconic acid in water with sodium borohydride at room temperature using the method described for 2-keto-3-deoxyheptonic acid by Weissbach (J. Biol. Chem. 234 (1959), 705-709), followed by oxidative decarboxylation of 3-deoxy-D-gluconate and 3-deoxy-D-mannonate with hydrogen peroxide as described e.g. in U.S. Pat. No. 3,312,683; Richards J. Chem. Soc. (1954), 3638-3640; Sowden J. Am. Chem. Soc. 76 (1954), 3541-3542.

In another preferred embodiment, the preparation of a mixture of DGN and DMN is carried out by hydrogenation of 2-dehydro-3-deoxy-D-gluconate in aqueous solution with 6% mol Nickel Raney catalyst or Platinum oxide at room temperature under a pressure of 6 bars.

In another embodiment of the invention, KDG or its salt is converted to 3-deoxy-D-glucosaminate (DGM) or 3-deoxy-D-mannosaminate (DMM) represented by formula (VIII) or the salts of these compounds

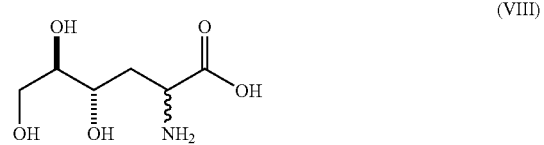

(VIII)

The products resulting from this reaction undergo (oxidative) decarboxylation, preferably using ninhydrin, to yield DRI. Production of a mixture of DGM and DMM or their salts takes place from KDG or its salts by reductive amination.

Preferably the preparation of 2-deoxy-D-ribose is carried out by non-stereoselective reductive amination of sodium or potassium 2-dehydro-3-deoxy-D-gluconate in aqueous solution with ammonia and sodium cyanoborohydride at room temperature, followed by oxidative decarboxylation of 3-deoxy-D-2-glucosaminate and 3-deoxy-D-2-mannosaminate with ninhydrin using the method described for the synthesis of 2-deoxy-D-allose by Shelton (J. Am. Chem. Soc. 118 (1996), 2117-2125; and Borch, J. Am. Chem. Soc. 93 (1971), 2897; Durrwachter, J. Am. Chem. Soc. 108 (1986), 7812 referenced therein).

Furthermore, the present invention provides a method for producing the compound of formula (III) (2-deoxy-D-ribose) by converting the compound of formula (I) or one of its salts (KDG) in one single step. Preferably this conversion is achieved through enzymatic catalysis. This conversion is preferably catalysed by a keto acid decarboxylase. Preferred keto acid decarboxylases are thiamin pyrophosphate (TPP) dependent keto acid decarboxylases. Examples of TPP dependent keto acid decarboxylases are pyruvate decarboxylase (EC 4.1.1.1), a benzoylformate decarboxylase (EC 4.1.1.7), an indolepyruvate decarboxylase (EC 4.1.1.74), a phosphonopyruvate decarboxylase, a sulfopyruvate decarboxylase (EC 4.1.1.79), an oxalyl-coenzymeA decarboxylase (EC 4.1.1.8), an oxoglutarate decarboxylase (EC 4.1.1.71) or a phenylpyruvate decarboxylase (EC 4.1.1.43). It could be shown that keto acid decarboxylases, e.g., pyruvate decarboxylase enzymes from different organisms, can convert KDG into 2-deoxy-D-ribose (see Examples 8 to 12). In principle any keto acid decarboxylase can be used in connection with the present invention.

In a preferred embodiment of the method according to the invention KDG is converted into 2-deoxy-D-ribose by use of an enzyme having pyruvate decarboxylase activity.

A pyruvate decarboxylase catalyses the following reaction:

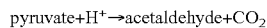

pyruvate+H$^+$→acetaldehyde+CO$_2$

Several pyruvate decarboxylases (PDC) have been characterized as well as the corresponding pdc genes, for instance PDC from *Zymomonas mobilis* (Genbank accession number MD19711; Neale et al., J. Bacteriol. 1987, 169:1024-1028), PDC from *Saccharomyces cerevisiae* (Genbank accession number NP013145; Candy et al., J. Gen. Microbiol. 1991, 137:2811-2815), PDC from *Acetobacter pasteurianus* (Genbank accession number MM21208; Raj et al., Arch. Microbiol. 2001, 176:443-451), PDC from *Zymobacter palmae* (Genbank accession number AAM49566; Raj et al., Appl. Environ. Microbiol. 2002, 68:2869-2876), PDC from *Sarcina ventriculi* (Genbank accession number ML18557; Lowe et al., J. Gen. Microbiol. 1992, 138:803-807). Many other pyruvate decarboxylases seems to occur in plants, fungi and bacteria as evidenced by the occurrence in these organisms of genes sharing sequence homologies with well-established pdc genes. Examples of such putative pyruvate decarboxylases are:

PDC from Plants:

*Arabidopsis thaliana* (Genbank accession number T48155)

*Echinochloa crus-galli* (Genbank accession number MM18119)

*Oryza sativa* (Genbank accession number NP922014)

*Rhizopus oryzae* (Genbank accession number AAM73540)

*Lotus corniculatus* (Genbank accession number M072533)

*Zea mays* (Genbank accession number BAA03354)

*Pisum sativum* (Genbank accession number CM91445)

Garden pea (Genbank accession number S65470)

*Nicotiana tabaccum* (Genbank accession number CM57447)

*Solanum tuberosum* (Genbank accession number BAC23043)

*Fragaria ananassa* (Genbank accession number ML37492)

*Cucumis melo* (Genbank accession number ML33553)

*Vitis vinifera* (Genbank accession number MG22488)

PDC from Fungi:

*Saccharum officinarum* (Genbank accession number CAB61763)

*Aspergillus orizae* (Genbank accession number MD16178)

*Aspergillus parasiticus* (Genbank accession number P51844)

*Saccharomyces cerevisiae* (Genbank accession number NP013145)

*Flammulina velutipes* (Genbank accession number MR00231)

*Saccharomyces kluyveri* (Genbank accession number AAP75899)

*Schizosaccharomyces pombe* (Genbank accession number CAB75873)

*Candida glabrata* (Genbank accession number MN77243)

*Neurospora crassa* (Genbank accession number JN0782)

*Pichia stipis* (Genbank accession number AAC03164)

*Kuyveromyces lactis* (Genbank accession number CM61155)

*Emericella nidulans* (Genbank accession number MB63012)

PDC from Prokaryotes:

*Mycobacterium bovis* (Genbank accession number CAD93738)

*Mycobacterium leprae* (Genbank accession number CAC31122)

*Mycobacterium tuberculosis* (Genbank accession number NP215368)

*Mycoplasma penetrans* (Genbank accession number NP758077)

*Clostridium acetobutylicum* (Genbank accession number NP149189)

*Acetobacter pasteurianus* (Genbank accession number AAM21208)

*Zymobacter palmae* (Genbank accession number AAM49566)

*Zymomonas mobilis* (Genbank accession number AAD19711)

*Sarcina ventriculi* (Genbank accession number AAL18557)

*Nostoc puncfiforme* (Genbank accession number ZP00110850)

Such enzymes can be easily produced by recombinant microorganisms overexpressing the corresponding gene. Examples of genes coding for TPP dependent keto acid decarboxylases are pdc from *Zymomonas mobilis* (Genbank accession number AF124349), pdc from *Saccharomyces cerevisiae* (Genbank accession number NC001144), pdc from *Acetobacter pasteurianus* (Genbank accession number AF368435), pdc from *Zymobacter palmae* (Genbank accession number AF474145), pdc from *Sarcina ventriculi* (Genbank accession number AF354297). Other pdc genes can be found at Genbank corresponding to the above list of putative pyruvate decarboxylases.

In a preferred embodiment the pyruvate decarboxylase is of eukaryotic origin, more preferably it is from yeast and most preferably it is from *Saccharomyces cerevisiae*. In a particularly preferred embodiment the pyruvate decarboxylase is the pyruvate decarboxylase from *S. cerevisiae* which has the amino acid sequence as shown in SEQ ID NO: 21 (see also GenBank accession number NP013145).

In another preferred embodiment the pyruvate decarboxylase is of prokaryotic origin, more preferably it is from an organism of the genus *Zymomonas* and most preferably from *Zymomonas mobilis*. In a particularly preferred embodiment the pyruvate decarboxylase is the pyruvate decarboxylase from *Z. mobilis* which has the amino acid sequence as shown in SEQ ID NO: 19 (see also GenBank accession number AAD19711).

In another preferred embodiment the prokaryotic pyruvate decarboxylase is from an organism of the genus *Acetobacter*, more preferably from the species *Acetobacter pasteurianus*. Particularly preferred the pyruvate decarboxylase is that of *A. pasteurianus* which shows the amino acid sequence as given in SEQ ID NO: 25 (see also GenBank accession number MM21208).

In a further preferred embodiment the pyruvate decarboxylase is from an organism of the genus *Zymobacter*, more preferably of the species *Zymobacter palmae*. Particularly preferred is a pyruvate decarboxylase from *Z. palmae* which shows the amino acid sequence given in SEQ ID NO: 29 (see also GenBank accession number AAM49566).

In another preferred embodiment of the method according to the invention KDG is converted into 2-deoxy-D-ribose by use of an enzyme having benzoylformate decarboxylase activity.

A benzoylformate decarboxylase catalyses the following reaction:

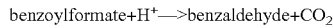

benzoylformate+H⁺→benzaldehyde+CO$_2$

A benzoylformate decarboxylase (BDC) from *Pseudomonas putida* (Genbank accessing number MC15502; Tsou et al., Biochemistry. 1990, 29:9856-9862) has been characterized as well as the corresponding gene mdlC (Genbank accessing number AY143338). This enzyme has been shown to decarboxylate both D and L isomers of 2-keto-4,5-dihydroxyvalerate into the respective isomers of 3,4-dihydroxybutanal (Niu et al., J. Am. Chem. Soc. 125 (2003), 12998-12999). Many other benzoylformate decarboxylases seems to occur in bacteria and archaebacteria as evidenced by the occurrence in these organisms of genes sharing sequence homologies with genes coding for well-established BDC. Examples of such putative benzoylformate decarboxylases are:

BDC from Bacteria:

*Pseudomonas aeruginosa* (Genbank accession number NP_253588)

*Rhodopseudomonas palustris* (Genbank accession number NP_946955)

*Streptomyces coelicolor* (Genbank accession number NP_631486)

*Chromobacterium violaceum* (Genbank accession number NP_902771)

*Bradyrhizobium japonicum* (Genbank accession number NP_774243)

BDC from Archaebacteria:

*Sulfolobus solfataricus* (Genbank accession number NP_343070)

*Thermoplasma acidophilum* (Genbank accession number NP_393976)

*Thermoplasma volcanium* (Genbank accession number NP_111716)

Such enzymes can be easily produced by recombinant microorganisms overexpressing the corresponding bdc gene. Such genes can be found at Genbank corresponding to the above list of putative benzoylformate decarboxylases.

Another example for a thiamine dependent decarboxylase which can be used in the method according to the invention is phosphonopyruvate decarboxylase. Several phosphonopyruvate decarboxylases (PPD) have been characterized as well as the corresponding genes, for instance PPD from *Bacteroides fragilis* (Genbank accession number AAG26466; Zhang et al., J. Biol. Chem. 2003, 278:41302-41308), PPD from *Streptomyces wedmorensis* (Genbank accession number BM32496; Nakashita et al., J. Antibiot. 1997, 50:212-219). Many other phosphonopyruvate decarboxylases seem to occur in bacteria as evidenced by the occurrence in these organisms of genes sharing sequence homologies with genes coding for well-established PPD. Examples of such putative phosphonopyruvate decarboxylases are: PPD from *Bacteroides thetaiotaomicron* (Genbank accession number NP_810632), PPD from *Amycolatopsis orientalls* (Genbank accession number CAB45023), PPD from *Clostridium tetani* E88 (Genbank accession number NP_782297), PPD from *Streptomyces viridochromogenes* (Genbank accession number CAA74722), PPD from *Streptomyces hygroscopicus* (Genbank accession number BM07055), PPD from *Streptomyces coelicolor* A3 (Genbank accession number NP_733715), *Streptomyces rishiriensis* (Genbank accession number MG29796), *Bordetella pertussis* (Genbank accession number CAE 41214. Such enzymes can be easily produced by recombinant microorganisms overexpressing the corresponding gene.

A further example of a thiamine dependent decarboxylases which can be used in the method according to the present invention is sulfopyruvate decarboxylase. A sulfopyruvate decarboxylases (SPD) from *Methanococcus jannaschii* (Graupner et al., J. Bacteriol. 2000. 182:4862-4867) consisting of two subunits ComD (Genbank accession number P58415) and ComE (Genbank accession number P58416) has been characterized as well as the corresponding genes. Many other sulfopyruvate decarboxylases seems to occur in archaebacteria and in bacteria as evidenced by the occurrence in these organisms of genes sharing sequence homologies with genes coding for well-established SPD.

Another further example of thiamine dependent decarboxylase which can be used in the method according to the present invention is indolepyruvate decarboxylase. Several indolepyruvate decarboxylases (IPD) have been characterized as well as the corresponding genes, for instance IPD from, *Enterobacter cloacae* (Genbank accession number BM14242; Scutz et al., 2003, Eur. J. Biochem. 270:2322-2331), IPD from *Azospirillum brasilense* (Genbank accession number MC36886; Costacurta et al., Mol. Gen. Genet. 1994, 243:463-472), IPD from *Erwinia herbicola* (Genbank accession number AAB06571; Brandl et al., Appl. Environ. Microbiol. 1996, 62:4121-4128). Many other indolepyruvate decarboxylases seem to occur in bacteria as evidenced by the occurrence in these organisms of genes sharing sequence homologies with genes coding for well-established IPD.

Still another further example of a thiamine dependent decarboxylases which can be used in the method according to the present invention is phenylpyruvate decarboxylase. A phenylpyruvate decarboxylase from yeast (Genbank accession number NP010668; Vuralhan et al., Appl. Environ. Microbiol. 2003, 69:4534-41) has been characterized as well as the corresponding gene ARO10 (Genbank accession number NC001136).

In a preferred embodiment of the method according to the invention in which the decarboxylation step is effected by an enzymatic reaction, the pH value is regulated by addition of an acid to be between pH 5 and pH 9, preferably between pH 6 and pH 8. In principle, any suitable acid can be used for this purpose. Preferred acids are HCl, $H_2SO_4$, D-gluconic acid or 2-dehydro-3-deoxy-D-gluconic acid.

Another aspect of the invention is a convenient and cost-effective method for preparing KDG either from D-gluconate (GCN) or from D-glucosaminate through the use of recombinant enzymes.

In a preferred embodiment of the method of the invention, the compound of formula (I) is produced in a preliminary step from a D-gluconate salt by the use of a D-gluconate dehydratase activity. Preferred salts are potassium or sodium D-gluconate. Preferably the D-gluconate dehydratase is encoded by a polynucleotide comprising the nucleotide sequence selected from the group consisting of:
(a) nucleotide sequences encoding a polypeptide comprising the amino acid sequence of SEQ ID No 2;
(b) nucleotide sequences comprising the coding sequence of SEQ ID No 1;
(c) nucleotide sequences encoding a fragment encoded by a nucleotide sequence of (a) or (b);
(d) nucleotide sequences hybridising with a nucleotide sequence of any one of (a) to (c); and
(e) nucleotide sequences which deviate from the nucleoside sequence of (d) as a result of degeneracy of the genetic code.

The enzymatic synthesis of KDG or its salts using D-gluconate dehydratase proceeds according to the following reaction: D-gluconate is converted into KDG by the elimination of one water molecule. The activity of a D-gluconate dehydratase has been characterized in different bacterial species e.g. in *Alcaligenes* (Kersters, Methods in Enzymology 42 (1975), 301-304); *Clostridium pasteurianum*, (Gottschalk, Methods in Enzymology 90 (1982), 283-287); *Thermoplasma acidophilum* (Budgen, FEBS Letters 196 (1986), 207-210) and *Sulfolobus solfataricus* (Nicolaus, Biotechnology Letters 8(7) (1986), 497-500). The preferred D-gluconate dehydratase was identified by screening several collection strains for D-gluconate dehydratase activity. The gene encoding a D-gluconate dehydratase, which was designated gcnD was selected from a genomic library of *Agrobacterium tumefaciens* strain C58, and further inserted in a multi copy vector optimised for expression. It was shown that a crude extract from *E. coli* cells over-expressing the gcnD gene catalysed the total conversion of D-gluconate into KDG (see Example 2).

In a further preferred embodiment of the method of the invention, the compound of formula (I) is produced in a preliminary step from D-glucosaminate by the use of a D-glucosaminate deaminase activity. Preferably the D-glucosaminate deaminase is encoded by a polynucleotide comprising the nucleotide sequence selected from the group consisting of:
(f) nucleotide sequences encoding a polypeptide comprising the amino acid sequence of SEQ ID No 4;
(g) nucleotide sequences comprising the coding sequence of SEQ ID No 3;
(h) nucleotide sequences encoding a fragment encoded by a nucleotide sequence of (a) or (b);
(i) nucleotide sequences hybridising with a nucleotide sequence of any one of (a) to (c); and
(j) nucleotide sequences which deviate from the nucleoside sequence of (d) as a result of degeneracy of the genetic code.

The enzymatic synthesis of KDG or its salts using D-glucosaminate deaminase proceeds according to the following reaction: D-glucosaminate is converted into KDG by the elimination of one molecule water and one molecule of ammonia. The activity of a D-glucosaminate deaminase has been characterized in different bacterial species e.g. in *Pseudomonas fluorescens* (Iwamoto, Agric. Biol. Chem. 53 (1989), 2563-2569) *Agrobacterium radiobacter* (Iwamoto, FEBS Letters 104 (1979), 131-134; Iwamoto, J. Biochem. 91 (1982), 283-289), and its requirement for $Mn^{2+}$ ion was shown (Iwamoto, Biosdi. Biotech. Biochem. 59 (1995), 408-411).

The preferred D-glucosaminate deaminase was identified by screening several collection strains for D-glucosaminate deaminase activity. The gene encoding a D-glucosaminate deaminase, which was designated gmaA was isolated from *Agrobacterium tumefaciens* strain C58 by cloning a gene annotated as a putative D-serine deaminase. The gmaA gene was further inserted in a multi copy vector optimised for expression. It was shown that a crude extract from *E. coli* cells over-expressing the gmaA gene catalysed the conversion of D-glucosaminate into KDG (see Example 4).

In a preferred embodiment the present invention relates to a method for producing a compound of formula III, in particular 2-deoxy-D-ribose, starting from D-gluconate or D-glucosaminate by enzymatic reactions which, in a first step, convert D-gluconate or D-glucosaminate into KDG as described above and, in a second step, convert KDG into 2-deoxy-D-ribose as described above.

Thus, the enzymatic conversion of D-gluconate into KDG can be achieved by the use of a D-gluconate dehydratase. The enzymatic conversion of D-glucosaminate into KDG can be achieved by the use of a D-glucosaminate deaminase. With respect to the preferred embodiments the same applies as has already been set forth above.

The enzymatic conversion of the resulting KDG into 2-deoxy-D-ribose can be achieved by the use of a keto acid decarboxylase. With respect to the preferred embodiments the same applies as has been set forth above.

The enzymatic two step method of converting D-gluconate or D-glucosaminate into 2-deoxy-D-ribose via KDG can be carried out in vitro by using cell extracts of cells expressing the corresponding enzymes or by using purified or partially purified enzymes. The enzymes can be enzymes which are naturally expressed in an organism or they may be recombinantly produced. Methods of preparing and isolating corresponding (recombinant) enzymes are well-known to the person skilled in the art.

In a preferred embodiment the enzymatic two step method of converting D-gluconate or D-glucosaminate into 2-deoxy-D-ribose via KDG is carried out in vivo, i.e. by using a suitable organism, which expresses the required enzyme activities. This organism may be any type of organism, preferably it is a cell, e.g. a plant, an animal, a fungal cell or a bacterial cell. Most preferably fungal or bacterial cells are used. Preferred fungi are yeasts, such as *Saccharomyces cerevisiae*; preferred bacterial cells are, e.g. *E. coli, Zymomonas mobilis, Zymobacter palmae, Acetobacter pasteurianus, Acinetobacter calcoaceticus, Agrobacterium tumefaciens* and *Bacillus subtilis*. The organism may be an organism which endogenously already expresses one of the enzymatic activities, i.e. a D-gluconate dehydratase or a D-glucosaminate deaminase for producing KDG, or a keto acid decarboxylase for converting KDG into 2-deoxy-D-ribose, and in which the respective other enzymatic activity is expressed due to the introduction of a corresponding exogenous nucleic acid molecule encoding the corresponding enzyme. Alternatively, the organism may also be an organism which naturally does not express the enzyme activities required for converting D-gluconate or D-glucosaminate into KDG and further into 2-deoxy-D-ribose and in which corresponding foreign nucleic acid molecules have been introduced encoding D-gluconate dehydratase or D-glucosaminate deaminase and a keto acid decarboxylase, respectively.

In a particularly, preferred embodiment the organism is an organism which does not express a KDG kinase (kdgK) activity. Such an enzyme activity would lead to a phosphorylation of KDG to KDPG, which in turn is cleaved by an aldolase into pyruvate and glyceraldehyde-phosphate, thereby diverting KDG into a different unwanted metabolic pathway. It is possible to use for the method according to the invention organisms which naturally do not express a kdgK gene. If the used organism naturally expresses a kdgK, means and methods are well-known to the skilled person to produce mutants or variants of such an organism in which the corresponding kdgk gene is inactivated.

If the described method according to the invention is carried out in vivo by using an organism which expresses a D-gluconate dehydratase for converting D-gluconate into KDG and a keto acid decarboxylase for converting KDG into 2-deoxy-D-ribose, this has the advantage that one can provide D-gluconate as a substrate in the culture medium used to culture the organism. D-gluconate is taken up by the organism and is converted into 2-deoxy-D-ribose.

In another particularly, preferred embodiment the organism is an organism which does not express a KDG aldolase (encoded by the eda gene in *E. coli*) activity. Such an enzyme activity would lead to cleavage of KDG into pyruvate and glyceraldehydes, thereby diverting KDG into a different unwanted metabolic pathway. It is possible to use for the method according to the invention organisms which naturally do not express an eda gene. If the used organism expresses an eda gene, means and methods are well-known to the skilled person to produce mutants or variants of such an organism in which the corresponding eda gene is inactivated.

In still another particularly, preferred embodiment the organism is an organism which does not express a 2-deoxy-D-ribose aldolase (encoded by the deoC gene in *E. coli*) activity. Such an enzyme activity would lead to cleavage of 2-deoxy-D-ribose into acetaldehyde and glyceraldehyde, thereby diverting 2-deoxy-D-ribose into a different unwanted metabolic pathway. It is possible to use for the method according to the invention organisms which naturally do not express a deoC gene. If the used organism expresses a deoC gene, means and methods are well-known to the skilled person to produce mutants or variants of such an organism in which the corresponding deoC gene is inactivated. For instance a deoC mutant of *E. coli* has been reported (Valentin-Hansen, EMBO J. 1 (1982), 317-322) as well as a method for deleting the deo operon in *E. coli* (Kaminski, J. Biol. Chem. 277 (2002), 14400-14407; Valentin-Hansen, Molec. Gen. Genet. 159 (1978), 191-202).

The present invention also relates to organism which are capable of enzymatically converting D-gluconate into KDG due to the expression of a D-gluconate dehydratase and/or of enzymatically converting D-glucosaminate into KDG due to the expression of a D-glucosaminate deaminase and which are furthermore capable of enzymatically converting KDG into 2-deoxy-D-ribose by a decarboxylation reaction catalysed by a keto acid decarboxylase. The organism may in principle be any suitable organism, preferably, it is a cell, e.g. a plant cell, an animal cell, a fungal cell or a bacterial cell. More preferably, it is a fungal or a bacterial cell. Preferred fungi are yeasts, e.g. *Saccharomyces cerevisiae*. Preferred bacteria are *Escherichia coli, Zymomonas mobilis, Zymobacter palmae, Acetobacter pasteurianus, Acinetobacter calcoaceticus, Agrobacterium tumefaciens* and *Bacillus subtilis*. In one aspect, the organism is an organism which already endogenously expresses a D-gluconate dehydratase or a D-glucosaminate deaminase and into which a foreign nucleic acid molecule has been introduced which encodes a keto acid decarboxylase which can catalyse the decarboxylation of KDG to 2-deoxy-D-ribose. With respect to the preferred embodiments of the keto acid decarboxylase the same applies as has been set forth previously.

In another aspect, the organism is an organism which already expresses a keto acid decarboxylase which is capable of converting KDG into 2-deoxy-D-ribose by a decarboxylation reaction but which does not naturally express a D-gluconate dehydratase or a D-glucosaminate deaminase, and into which a foreign nucleic acid molecule has been introduced which encodes a D-gluconate dehydratase and/or which encodes a D-glucosaminate deaminase. I.e. the organism can be genetically modified so as to express a D-gluconate dehydratase or a D-glucosaminate deaminase or both enzymes.

In a further aspect, the organism is an organism, which naturally does not express a D-gluconate dehydratase, a D-glucosaminate deaminase and a keto acid decarboxylase which is capable of converting KDG by decarboxylation into 2-deoxy-D-ribose, and into which foreign nucleic acid molecules have been introduced encoding a D-gluconate dehydratase or a D-glucosaminate deaminase, or both, and a nucleic acid molecule which encodes a keto acid decarboxylase which is capable of converting KDG into 2-deoxy-D-ribose by decarboxylation.

With respect to the preferred embodiments of the D-gluconate dehydratase, the D-glucosamine deaminase and the keto acid decarboxylase to be expressed in the organisms according to the invention, the same applies which has been set forth above in connection with the method according to the invention.

In a particularly preferred embodiment the organism according to the invention does not express a KDG kinase (kdgk) activity. It can either be an organism which naturally does not express kdgk or it can be an organism which naturally expresses a kdgK but in which the corresponding gene has been inactivated, e.g. by gene disruption or other suitable methods well-known to the person skilled in the art.

The present invention also relates to the use of an enzyme having keto acid decarboxylase activity or of a polynucleotide encoding such an enzyme in a method for converting KDG into 2-deoxy-D-ribose. With respect to the preferred embodiments the same applies as has already been set forth in connection with the method according to the present invention.

These and other embodiments are disclosed and encompassed by the description and examples of the present invention. The disclosure content of any references cited above or below is herewith incorporated into the present application. Further literature concerning any one of the methods, uses and compounds to be employed in accordance with the present invention may be retrieved from public libraries, using for example electronic devices. For example the public database "Medline" may be utilized which is available on the Internet. Further databases and addresses, such as that of the National Center for Biotechnology Information ("ncbi") and the Friedrich Miescher Institute for Biomedical Research are known to the person skilled in the art and can also be obtained using, e.g., readily-available search engines such as that provided by Google. An overview of patent information in biotechnology and a survey of relevant sources of patent information useful for retrospective searching and for current awareness is given in Berks, TIBTECH 12 (1994), 352-364.

Furthermore, the term "and/or" when occurring herein includes the meaning of "and", "or" and "all or any other combination of the elements connected by said term".

EXAMPLES

Example 1

Cloning of a Gene Encoding a D-Gluconate Dehydratase from *Agrobacterium tumefaciens* Strain C58 (CIP 104333)

*Agrobacterium tumefaciens* strain C58 (CIP 104333) was obtained from Institut Pasteur Collection (CIP, Paris, France). Chromosomal DNA was extracted and a D-gluconate dehydratase gene was amplified by PCR according to standard protocols using the following primers:

```
5'-CCCTTAATTAATGACGACATCTGATAATCTTC-3',
depicted in SEQ ID N° 5;

5'-TTTGCGGCCGCTTAGTGGTTATCGCGCGGC-3',
depicted in SEQ ID N° 6;

5'-CCCGGTACCATGACGACATCTGATAATCTTC-3',
depicted in SEQ ID N° 7;
```

A first DNA fragment amplified using the two primers depicted in SEQ ID No 5 and SEQ ID No 6, was ligated into a pUC18-derived vector previously digested by PacI and NotI to yield the plasmid pVDM80. A second DNA fragment amplified using the two primers depicted in SEQ ID No 6 and SEQ ID No 7, was ligated into a pET29a vector (Novagen) previously digested by KpnI and NotI to yield the plasmid pVDM82. The nucleotide sequence of the cloned gene is depicted in SEQ ID No 1 and the sequence of the polypeptide encoded by this gene is depicted in SEQ ID No 2.

Example 2

Expression of a D-Gluconate Dehydratase Activity in *Escherichia coli* and Preparation of 2-dehydro-3-deoxy-D-gluconate from D-gluconate Competent cells of *E. coli* BL21 were transformed with the pVDM82 plasmid constructed as described in example 1 yielding strain +1289. Strain +1289 was cultivated at 30° C. in Luria-Bertani (LB) medium (Difco) containing 30 mg/l kanamycin until OD(600 nm) reached a value of 0.6. Then isopropyl-β-D-thiogalactopyranoside (IPTG) was added to a 0.5 mM final concentration. After a further cultivation period of 2 hours and 30 minutes, cells were collected by centrifugation and washed once with 20 mM sodium phosphate buffer pH 7.2. A cell extract was prepared by suspending about 5 g of cells in 10 ml of Tris-HCl 50 mM pH 8.5 buffer containing 10000 units lysozyme (Ready-Lyse, Epicentre, Madison, Wis.) and 1 mM EDTA, and incubating the suspension at 30° C. for 15 minutes. Then 10000 kUnits deoxyribonuclease I (DNase I, Sigma) as well as 5 mM $MgCl_2$ were added to the preparation which was incubated at 30° C. for an additional period of 15 minutes. The cell extract thus obtained was kept frozen at −20° C. before use.

1.5 ml of the cell extract was mixed with 2M sodium or potassium D-gluconate in a total volume of 10 ml. This preparation was incubated at 37° C. after the pH has been adjusted to 8.5. The progression of 2-dehydro-3-deoxy-D-gluconate (KDG) synthesis was followed by analysing aliquots taken after increasing periods of incubation. Several dilution parts of these aliquots were deposited on silica plates and chromatographied in the following solvent system: isopropanol/water (90/10). A yellow spot of KDG (Rf~0.40) was detected after revelation with p-anisaldehyde. KDG was also quantitated using a spectrophotometric assay based on the reaction with semicarbazide hydrochloride as described by Mac Gee (J. Biol. Chem. 1954. 210, 617-626). Typically, after a 30 h period of incubation and using the spectrophotometric assay, KDG concentration ranged from 1.5 to 2 M.

The sodium or potassium 2-dehydro-3-deoxy-D-gluconate solution thus obtained could be used as such for further synthetic steps. 2-Dehydro-3-deoxy-D-gluconic acid could also be prepared from such a solution applying published protocols (Bender, Anal. Biochem. 1974. 61, 275-279). A crude preparation of a mixture of 2-dehydro-3-deoxy-D-gluconic acid and KCl could also be obtained by adding one equivalent of HCl to a potassium 2-dehydro-3-deoxy-D-gluconate solution which was then evaporated.

Example 3

Cloning of a Gene Encoding a D-Glucosaminate Deaminase from *Agrobacterium tumefaciens* Strain C58 (CIP 104333)

*Agrobacterium tumefaciens* strain C58 (CIP 104333) was obtained from Institut Pasteur Collection (CIP, Paris, France). Chromosomal DNA was extracted and a D-glucosaminate deaminase gene was amplified by PCR according to standard protocols using the following primers:

```
5'-CCCTTAATTAATGCAGTCTTCTTCAGCTCTTC-3',
depicted in SEQ ID N° 8;

5'-TTTGCGGCCGCCTAGTGAAAGAAGGTTGTGTAGAT-3',
depicted in SEQ ID N° 9;

5'-AAATCATGACTATGCAGTCTTCTTCAGCTCTTCG-3',
depicted in SEQ ID N° 10;

5'-TATAGATCTCTAGTGAAAGAAGGTTGTGTAGAT-3',
depicted in SEQ ID N° 11;
```

A first DNA fragment amplified using the two primers depicted in SEQ ID No 8 and SEQ ID No 9, was ligated into a pUC18-derived vector previously digested by PacI and NotI to yield the plasmid pKDGb1. A second DNA fragment amplified using the two primers depicted in SEQ ID No 10 and SEQ ID No 11, was ligated into a pQE60 vector (Qiagen) previously digested by BspH1 and BglII to yield the plasmid pEP18. The nucleotide sequence of the cloned gene is depicted in SEQ ID No 3 and the sequence of the polypeptide encoded by this gene is depicted in SEQ ID No 4.

Example 4

Expression of a D-glucosaminate deaminase activity in *Escherichia coli* and preparation of 2-dehydro-3-deoxy-D-gluconic acid from D-glucosaminate Competent cells of. *E. coli* MG1655 were transformed with the pEP18 plasmid constructed as described in example 1 and pREP4 (Qiagen) yielding strain +1068. Strain +1068 was cultivated at 37° C. in LB medium containing 30 mg/l kanamycin and 100 mg/l ampicillin until OD(600 nm) reached a value of 0.6. Then IPTG was added to a 0.5 mM final concentration. After a further cultivation period of 2 hours and 30 minutes, cells were collected by centrifugation and washed once with 20 mM sodium phosphate buffer pH 7.2. A cell extract was prepared using the protocol described in example 2.

2 ml of the cell extract was mixed with 100 mM sodium or potassium D-glucosaminate and 0.1 mM pyridoxal phosphate in a total volume of 5 ml. This preparation was incubated at 37° C. after the pH has been adjusted to 7.5.

The progression of 2-dehydro-3-deoxy-D-gluconate (KDG) synthesis was followed using the protocols described in example 2. Typically, after a 30 h period of incubation and using the spectrophotometric assay described in example 2, KDG concentration ranged from 50 to 100 mM.

Example 5

Preparation of 2-deoxy-D-ribonate from 2-dehydro-3-deoxy-D-gluconate 0.5 ml of a 31% hydrogen peroxyde solution were added to 5 ml of a 1M potassium 2-dehydro-3-deoxy-D-gluconate (KDG) solution at 25° C. The progression of KDG decarboxylation was followed both by the observation of bubbles resulting from the release of carbon dioxide and by the disappearance of KDG using the thin layer chromatography protocol described in example 2. Typically, after a 3 h period of reaction the concentration of residual KDG was less than 10 mM.

Example 6

Preparation of 2-deoxy-D-ribitol from 2-deoxy-D-ribonolactone 0.2 g of Rhodium (5% on carbon) catalyst was added to an aqueous solution of 1 g 2-deoxy-D-ribonolactone prepared following a method described by Deriaz (J. Chem. Soc. (1949), 1879-1883) for the synthesis of 2-deoxy-L-ribonolactone. Hydrogenation of 2-deoxy-D-ribonolactone was performed at 130° C. under a pressure of 80 bars. The solution obtained after filtration of the reaction mixture was evaporated. The residue was dissolved in ethyl acetate and further purified by chromatography on a silica column. The solvent was removed in vacuo leading to a yellow oil (yield 85%). The compound thus obtained was identical with 2-deoxy-D-ribitol obtained by reduction of 2-deoxy-D-ribose as described by Rabow (J. Am. Chem. Soc. 122 (1999), 3196-3203).

Example 7

Preparation of 1-N-morpholino-3,4,5-trihydroxypentene-1 from 2-dehydro-3-deoxy-D-gluconate 2 g of 2-dehydro-3-deoxy-D-gluconic acid were suspended in 150 ml benzene. 1.1 ml morpholine and 100 mg p-toluenesulfonic acid were added to the suspension and the reaction mixture was refluxed for 3 hours. Water formed by this reaction was removed by distillation. Benzene was decanted. Solid compounds attached to the vessel were collected, washed with acetone and dried. The main compound present in this preparation (yield 40%) was further purified by column chromatography on a silica column using a gradient of methanol in chloroform. Fractions containing 1-N-morpholino-3,4,5-trihydroxypentene-1 were pooled and solvent was removed in vacuo.

$^1$H-NMR ($D_2O$): δ=3.15 ppm (4H, t, morpholine), 3.8 ppm (4H, t, morph oline), 3.4 to 4 ppm, (4H, m, 5a-H, 5b-H, 4-H, 3-H), 6.3 and 6.8 ppm (2H, 2d, 1-H and 2-H, J=4 Hz).

Example 8

Cloning of a Gene Encoding a Pyruvate Decarboxylase from *Zymomonas mobilis*

*Zymomonas mobilis* strain B-806 (CIP 102538T) was obtained from Institut Pasteur Collection (CIP, Paris, France). Chromosomal DNA was extracted and a pyruvate decarboxylase gene was amplified by PCR according to standard protocols using the following primers:

```
5'-GCGTTAATTAATGAGTTATACTGTCGGTACC-3',
depicted in SEQ ID N° 12;

5'-TATGCGGCCGCTTAGAGGAGCTTGTTAACAGG-3',
depicted in SEQ ID N° 13;
```

The DNA fragment amplified using the two primers depicted in SEQ ID No 12 and SEQ ID No 13, was ligated either into pSP100 or into pEVL5 (respectively a pUC18-derived or a pQE70-derived vector as described below) previously digested by PacI and NotI to yield respectively plasmid pEVL107 and plasmid pEVL420. The nucleotide sequence of the cloned gene as well as the encoded sequence of the corresponding polypeptide can be found at GenBank (accession number AF124349) and is shown in SEQ ID NO: 18 and SEQ ID NO: 19, respectively.

Plasmid pSP100 was obtained by introducing a ribosomal binding site, a PacI and a NotI restriction sites into a pUC18 vector previously digested by EcoRI and BamHI using standard protocols. The complete nucleotide sequence of pSP100 is depicted in SEQ ID No 14.

Plasmid pEVL5 was obtained by introducing a ribosomal binding site, a PacI and a NotI restriction sites into a pQE70 vector (Qiagen) previously digested by EcoRI and BamHI using standard protocols. The complete nucleotide sequence of pEVL5 is depicted in SEQ ID No 15.

Example 9

Cloning of a Gene Encoding a Pyruvate Decarboxylase from *Saccharomyces cerevisiae*

Chromosomal DNA was extracted from *Saccharomyces cerevisiae* strain S288C (ATCC 204508) and a pyruvate decarboxylase gene was amplified by PCR according to standard protocols using the following primers:

```
5'-ATATTTAATTAATGTCTGAAATTACTTTGG-3',
depicted in SEQ ID N° 16;

5'-ATATGCGGCCGCTTATTGCTTAGCGTTGGT-3',
depicted in SEQ ID N° 17;
```

The DNA fragment amplified using the two primers depicted in SEQ ID No 16 and SEQ ID No 17, was ligated either into pSP100 or into pEVL5 (respectively a pUC18-derived or a pQE70-derived vector as described in example 8) previously digested by PacI and NotI to yield respectively plasmid pVDM61 and plasmid pEVL419. The nucleotide sequence of the cloned gene as well as the encoded sequence of the corresponding polypeptide can be found at GenBank (accession number NC001144) and is shown in SEQ ID NO: 20 and SEQ ID NO: 21, respectively.

Example 10

Expression of a Pyruvate Decarboxylase Activity in *Escherichia coli* and Enzymatic Synthesis of 2-deoxy-D-ribose from 2-dehydro-3-deoxy-D-gluconate Expression of Pyruvate Decarboxylase and Preparation of Cell-Free Extracts Competent cells of *E. coli* MG1655 strain were transformed with either pEVL107 or pVDM61 (constructed as described in examples 8 and 9) yielding respectively strain +1735 and strain +844. These strains were cultivated at 37° C. in Luria-Bertani (LB) medium (Difco) containing 100 mg/l ampicillin until OD(600 nm) reached a value around 1.5.

Competent cells of *E. coli* MG1655 strain harbouring pREP4 plasmid (Qiagen) were transformed with either pEVL420 or pEVL419 (constructed as described in Examples 8 and 9) yielding respectively strain +3150 and +3148. These strains were cultivated at 37° C. in Luria-Bertani (LB) medium (Difco) containing 100 mg/l ampicillin and 30 mg/l kanamycin until OD(600 nm) reached a value of 0.6. Then isopropyl-β-D-thiogalactopyranoside (IPTG) was added to a 0.5 mM final concentration. After a further cultivation period of 2 hours and 30 minutes, cells were collected by centrifugation and washed once with 20 mM sodium phosphate buffer pH 7.2.

For each strain a cell-free extract was prepared using the same protocol as described in Example 2. Then crude cell-free extracts were passed through a PD-10 column (Amersham) equilibrated with 50 mM Tris-acetate buffer pH 6 and stored at −20° C.

Enzymatic Synthesis of 2-deoxy-D-ribose from 2-dehydro-3-deoxy-D-gluconate 1.0 ml of cell-free extract was mixed with 20 mM sodium 2-dehydro-3-deoxy-D-gluconate, 0.5 mM thiamine pyrophosphate and 5 mM $MgCl_2$ in a total volume of 1.5 ml of 50 mM tris-acetate buffer pH 6. The progression of 2-deoxy-D-ribose (DRI) synthesis was followed by analysing aliquots taken after increasing periods of Incubation at 37° C. About 1 µl of each aliquot which had been previously concentrated five-fold by evaporation was deposited on a silica plate and chromatographied in the following solvent system: butanol/triethylamine/water (10/2/5). A blue spot of DRI (Rf ~0.50) was detected after revelation with orcinol when using cell-free extracts of either strain +3150 or +3148 after a period of incubation of 65 hours. The crude preparation containing the spot corresponding to DRI was concentrated and passed through a 1.5 ml silica column equilibrated with isopropanol. The fractions containing the expected DRI compound were pooled, concentrated and the resulting sample analysed by mass spectrometry. The results of such an analysis confirmed the identity of the isolated compound with DRI, and the production of DRI from KDG catalysed by pyruvate decarboxylase either from *Zymomonas mobilis* or from *Saccharomyces cerevisiae*.

Example 11

Cloning of a Gene Encoding a Pyruvate Decarboxylase from *Acetobacter pasteurianus*, Expression of Encoded Pyruvate Decarboxylase Activity in *Escherichia coli* and Enzymatic Synthesis of 2-deoxy-D-ribose from 2-dehydro-3-deoxy-D-gluconate

*Acetobacter pasteurianus* strain NCIB 8618 (DSMZ 2347) was obtained from DSMZ Collection (Deutsche Sammiung von Mikroorganismen und Zellkulturen GmbH, Braunschweig, Germany). Chromosomal DNA was extracted from the cells and a pyruvate decarboxylase gene was amplified by PCR according to standard protocols using the following primers:

```
5'-TCTTTAATTAATGGGTTGTCCGTCATTCATATA-3',
depicted in SEQ ID N° 22;

5'-CTAAAGCTTTTAGGCCAGAGTGGTCTTGCGCG-3',
depicted in SEQ ID N° 23;
```

The DNA fragment amplified using the two primers depicted in SEQ ID No 22 and SEQ ID No 23, was ligated either into pSP100 or into pEVL5 (respectively a pUC18-derived or a pQE70-derived vector as described in example 8) previously digested by PacI and NotI to yield respectively plasmid pEVL541 and plasmid pEVL560. The nucleotide sequence SEQ ID No 24 of the cloned gene as well as the encoded sequence of the corresponding polypeptide SEQ ID No 25 can be found at GenBank (accession number AF36843.5).

Competent cells of *E. coli* MG1655 strain were transformed with pEVL541 yielding strain +3559. Competent cells of *E. coli* MG1655 strain harbouring pREP4 plasmid (Qiagen) were transformed with pEVL560 yielding strain +3924. These strains were cultivated and cell-free extracts were prepared as described in Example 10. Cell-free extracts were incubated with KDG and the progression of 2-deoxy-D-ribose (DRI) synthesis was followed as described in Example 10. A spot corresponding to DRI was observed indicating that pyruvate decarboxylase from *Acetobacter pasteurianus* was able to decarboxylate KDG into DRI.

Example 12

Cloning of a Gene Encoding a Pyruvate Decarboxylase from *Zymobacter palmae*, Expression of Encoded Pyruvate Decarboxylase Activity in *Escherichia coli* and Enzymatic Synthesis of 2-deoxy-D-ribose from 2-dehydro-3-deoxy-D-gluconate

*Zymobacter palmae* strain T109 (DSMZ10491) was obtained from DSMZ Collection (Deutsche Sammiung von Mikrokulturen und Zellkulturen GmbH, Braunschweig, Germany). Chromosomal DNA was extracted from the cells and a pyruvate decarboxylase gene was amplified by PCR according to standard protocols using the following primers:

```
5'-ATCTTAATTAATGTATACCGTTGGTATGTACT-3',
depicted in SEQ ID N° 26;

5'-TATGCGGCCGCTTACGCTTGTGGTTTGCGAGAGT-3',
depicted in SEQ ID N° 27.
```

The DNA fragment amplified using the two primers depicted in SEQ ID No 26 and SEQ ID No 27, was ligated either into pSP100 or into pEVL5 (respectively a pUC18-derived or a pQE70-derived vector as described in example 8) previously digested by PacI and NotI to yield respectively plasmid pEVL546 and plasmid pEVL561. The nucleotide sequence of the cloned gene as well as the encoded sequence of the corresponding polypeptide is shown in SEQ ID NOs: 28 and 29, respectively and can be found at GenBank (accession number AF474145).

Competent cells of *E. coli* MG1655 strain were transformed with pEVL546 yielding strain +3568. Competent cells of *E. coli* MG1655 strain harbouring pREP4 plasmid (Qiagen) were transformed with pEVL560 yielding strain +3923. These strains were cultivated and cell-free extracts were prepared as described in Example 10. Cell-free extracts were incubated with KDG and the progression of 2-deoxy-D-ribose (DRI) synthesis was followed as described in Example 10. A spot corresponding to DRI was observed indicating that pyruvate decarboxylase from *Zymobacter palmae* was able to decarboxylate KDG into DRI.

Example 13

Cloning of a Gene Encoding a Benzoylformate Decarboxylase from *Pseudomonas putida*, Expression of Encoded Benzoylformate Decarboxylase Activity in *Escherichia coli* and Enzymatic Synthesis of 2-deoxy-D-ribose from 2-dehydro-3-deoxy-D-gluconate

*Pseudomonas putida* strain Migula (DSMZ 291) was obtained from DSMZ Collection (Deutsche Sammiung von Mikroorganismen und Zellkulturen GmbH, Braunschweig, Germany). Chromosomal DNA was extracted, from and a benzoylformate decarboxylase gene was amplified by PCR according to standard protocols using the following primers:

```
5'-CTATTAATTAATGGCTTCGGTACACGGCACCA-3',
depicted in SEQ ID N° 30;

5'-TATGCGGCCGCTTACTTCACCGGGCTTACGGTGC-3',
depicted in SEQ ID N° 31;
```

The DNA fragment amplified using the two primers depicted in SEQ ID No 30 and SEQ ID No 31, was ligated either into pSP100 or into pEVL5 (respectively a pUC18-derived or a pQE70-derived vector as described in example 8) previously digested by PacI and NotI to yield respectively plasmid pEVL681 and plasmid pEVL670. The nucleotide sequence SEQ ID No 32 of the cloned gene as well as the encoded sequence of the corresponding polypeptide SEQ ID No 33 can be found at GenBank (accessing number AY143338).

Competent cells of *E. coli* MG1655 strain were transformed with pEVL681 yielding strain +4050. Competent cells of *E. coli* MG1655 strain harbouring pREP4 plasmid (Qiagen) were transformed with pEVL670 yielding strain +3927. Those strains were cultivated and cell-free extracts were prepared as described in example 10. Cell-free extracts were incubated with KDG and the progression of 2-deoxy-D-ribose (DRI) synthesis was followed as described in example 10. A spot corresponding to DRI was observed indicating that benzoylformate decarboxylase from *Pseudomonas putida* was able to decarboxylate KDG into DRI.

Preparative Enzymatic Synthesis of 2-deoxy-D-ribose

100 µl of cell-free extract from strain +3927 (containing 2.5 mg of bacterial proteins) were mixed with 300 mM sodium 2-dehydro-3-deoxy-D-gluconate, 0.5 mM thiamine pyrophosphate and 5 mM $MgCl_2$ in a total volume of 0.5 ml of 80 mM potassium phosphate buffer pH 6. After a period of incubation of 16 and 40 hours, few µl of a solution of HCl 2N were added to the incubation mixture until the pH reached a value of 6. The progression of 2-deoxy-D-ribose (DRI) synthesis was also followed by analysing aliquots taken after increasing periods of incubation at 37° C. About 1 µl of each aliquot was deposited on a silica plate and chromatographed as described in example 10. The concentration of 2-deoxy-D-ribose was estimated to be about 200 mM by comparison with standard solutions. $^{13}C$ NMR analysis of the crude mixture confirmed that the compound formed from 2-dehydro-3-deoxy-D-gluconate was 2-deoxy-D-ribose, and that the concentration of 2-deoxy-D-ribose was closed to 25 g/l. Another preparative enzymatic synthesis was performed in the same conditions except that no addition of acid was made along the incubation period. In those conditions, the concentration of 2-deoxy-D-ribose was closed to 10 g/l, far lower than the concentration reached in the preceding experiment for which the pH had been controlled and regularly adjusted to a value of 6.

Example 14

Enzymatic Synthesis of 2-deoxy-D-ribose from D-gluconate

One pot enzymatic synthesis of 2-deoxy-D-ribose from D-gluconate was achieved as follows, using D-gluconate dehydratase encoded by gcnD gene of *Agrobacterium tumefaciens* and pyruvate decarboxylase from *Zymomonas mobilis*:

50 µl of cell-free extract from strain +1289 (containing 1.5 mg of bacterial proteins) and 400 µl of cell-free extract from strain +3150 (containing 17 mg of bacterial proteins after concentration by ultrafiltration) prepared as described respectively in example 2 and in example 10, were mixed with 50 mM potassium D-gluconate, 0.5 mM thiamine pyrophosphate and 5 mM $MgCl_2$ in a total volume of 0.5 ml of 50 mM N-(2-hydroxyethyl)piperazine-N'-(2-ethanesulfonic acid) (HEPES) buffer pH 7. The progression of 2-deoxy-D-ribose (DRI) synthesis was also followed by analysing aliquots taken after increasing periods of incubation at 37° C. After a period of incubation of 18 hours, about 1 µl of the incubation mixture was deposited on a silica plate and chromatographed as described in example 10. The concentration of 2-deoxy-D-ribose was estimated to be about 1 µl by comparison with standard solutions.

The invention claimed is:

1. A method for producing 2'-deoxynucleosides or 2'-deoxynucleoside precursors, wherein said 2'-deoxynucleoside precursors are 2-deoxy-D-ribose (DRI) or carbohydrate compounds which can be converted into the 2-deoxy-D-ribosyl moiety of 2'-deoxynucleosides, including 1-phospho-2-deoxy-D-ribose, 5-phospho-2-deoxy-D-ribose, 2-deoxy-D-ribitol, 2-deoxy-D-ribonic acid, and 2-deoxy-D-ribono-1,4-lactone, by decarboxylating a compound of formula (I), or its salts,

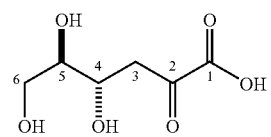

(I)

or a protected form thereof wherein one or more of the hydroxyl groups at positions 4, 5, and/or 6 are protected by a protection group in a process comprising a decarboxylation step; wherein the decarboxylation step is effected by an enzymatic reaction comprising a single step, and the enzymatic reaction is catalyzed by an enzyme having keto acid decarboxylase activity.

2. The method of claim 1, wherein the decarboxylation step cleaves the C1—C2 bond of the compound of formula (I) or its salts or a protected form thereof.

3. The method of claim 1, wherein the decarboxylation step is directly carried out on the compound of formula (I) or its salts or a protected form thereof.

4. The method of claim 1, wherein the enzyme having keto acid decarboxylase activity is a thiamine pyrophosphate (TPP) dependent keto acid decarboxylase.

5. The method of claim 4, wherein the TPP dependent keto acid decarboxylase is a pyruvate decarboxylase (EC 4.1.1.1), a benzoylformate decarboxylase (EC 4.1.1.7), an indolepyruvate decarboxylase (EC 4.1.1.74), a phosphonopyruvate decarboxylase, a sulfopyruvate decarboxylase (EC 4.1.1.79); an oxalyl-coenzyme A decarboxylase (EC 4.1.1.8), an oxoglutarate decarboxylase (EC 4.1.1.71) or a phenylpyruvate decarboxylase (EC 4.1.1.43).

6. The method of claim 5, wherein the pyruvate decarboxylase is of eukaryotic origin.

7. The method of claim 6, wherein the eukaryotic organism is a yeast organism.

8. The method of claim 7, wherein the yeast is *Saccharomyces cerevisiae*.

9. The method of claim 5, wherein the pyruvate decarboxylase is of prokaryotic origin.

10. The method of claim 9, wherein the prokaryotic organism is of the genus *Zymomonas, Zymobacter* or *Acetobacter*.

11. The method of claim 10, wherein the organism is of the species *Zymomonas mobilis, Zymobacter plamae* or *Acetobacter pasteurianus*.

12. The method of claim 5, wherein the benzoylformate decarboxylase is of prokaryotic origin.

13. The method of claim 12, wherein the prokaryotic organism is of the genus *Pseudomonas*.

14. The method of claim 13, wherein the organism is of the species *Pseudomonas putida*.

15. The method of claim 1, wherein the pH is regulated by addition of an acid between pH 5 and pH 9.

16. The method of claim 15, wherein the acid is HCl, $H_2SO_4$, D-gluconic acid or 2-dehydro-3-deoxy-D-gluconic acid.

17. The method of claim 1, comprising the preliminary step of producing the compound of formula (I) from D-gluconate or a D-gluconate salt by the use of a gluconate dehydratase activity.

18. The method of claim 17, wherein the D-gluconate salt is potassium or sodium D-gluconate.

19. The method of claim 17, wherein the gluconate dehydratase is encoded by a polynucleotide comprising the nucleotide sequence selected from the group consisting of:
 (a) nucleotide sequences encoding a polypeptide comprising the amino acid sequence of SEQ ID No 2;
 (b) nucleotide sequences comprising the coding sequence of SEQ ID No 1;
 (c) nucleotide sequences encoding a fragment encoded by a nucleotide sequence of (a) or (b);
 (d) nucleotide sequences hybridising with a nucleotide sequence of any one of (a) to (c); and
 (e) nucleotide sequences which deviate from the nucleoside sequence of (d) as a result of degeneracy of the genetic code.

20. The method of claim 1, comprising the preliminary step of producing the compound of formula (I) from D-glucosaminate by the use of a glucosaminate deaminase activity.

21. The method of claim 20, wherein the glucosaminate deaminase is encoded by a polynucleotide comprising the nucleotide sequence selected from the group consisting of:
 (a) nucleotide sequences encoding a polypeptide comprising the amino acid sequence of SEQ ID No 4;
 (b) nucleotide sequences comprising the coding sequence of SEQ ID No 3;
 (c) nucleotide sequences encoding a fragment encoded by a nucleotide sequence of (a) or (b);
 (d) nucleotide sequences hybridising with a nucleotide sequence of any one of (a) to (c); and
 (e) nucleotide sequences which deviate from the nucleoside sequence of (d) as a result of degeneracy of the genetic code.

* * * * *

SEQUENCE LISTING

<160> NUMBER OF SEQ ID NOS: 17

<210> SEQ ID NO 1
<211> LENGTH: 1812
<212> TYPE: DNA
<213> ORGANISM: Agrobacterium tumefaciens
<220> FEATURE:
<221> NAME/KEY: CDS
<222> LOCATION: (1)..(1809)
<223> OTHER INFORMATION:

<400> SEQUENCE: 1

| | | | | | | | | | | | | | | | | |
|---|---|---|---|---|---|---|---|---|---|---|---|---|---|---|---|---|
| atg | acg | aca | tct | gat | aat | ctt | cct | gca | act | cag | ggc | aag | ctc | cgt | tcg | 48 |
| Met | Thr | Thr | Ser | Asp | Asn | Leu | Pro | Ala | Thr | Gln | Gly | Lys | Leu | Arg | Ser | |
| 1 | | | | 5 | | | | | 10 | | | | | 15 | | |
| cgc | gcc | tgg | ttc | gac | aac | cca | gcc | aat | gcg | gac | atg | acc | gcg | ctt | tat | 96 |
| Arg | Ala | Trp | Phe | Asp | Asn | Pro | Ala | Asn | Ala | Asp | Met | Thr | Ala | Leu | Tyr | |
| | | | 20 | | | | | 25 | | | | | 30 | | | |
| ctc | gag | cgt | tac | atg | aac | ttc | ggt | ctc | agc | cag | gcc | gag | ctt | cag | tcc | 144 |
| Leu | Glu | Arg | Tyr | Met | Asn | Phe | Gly | Leu | Ser | Gln | Ala | Glu | Leu | Gln | Ser | |
| | | 35 | | | | | 40 | | | | | 45 | | | | |
| gac | cgc | ccg | att | atc | ggt | att | gcg | cag | acc | ggt | tcc | gac | ctt | tcg | ccc | 192 |
| Asp | Arg | Pro | Ile | Ile | Gly | Ile | Ala | Gln | Thr | Gly | Ser | Asp | Leu | Ser | Pro | |
| | 50 | | | | | 55 | | | | | 60 | | | | | |
| tgc | aac | cgt | cat | cat | ctg | gaa | ctc | gcc | aac | cgt | ctg | cgt | gaa | ggc | att | 240 |
| Cys | Asn | Arg | His | His | Leu | Glu | Leu | Ala | Asn | Arg | Leu | Arg | Glu | Gly | Ile | |
| 65 | | | | | 70 | | | | | 75 | | | | | 80 | |
| cgt | gaa | gcc | ggc | ggc | atc | gcc | atc | gaa | ttc | ccg | gtg | cat | ccg | atc | cag | 288 |
| Arg | Glu | Ala | Gly | Gly | Ile | Ala | Ile | Glu | Phe | Pro | Val | His | Pro | Ile | Gln | |
| | | | | 85 | | | | | 90 | | | | | 95 | | |
| gaa | acc | ggt | aag | cgt | ccg | aca | gcg | ggc | ctt | gat | cgc | aac | ctg | gct | tac | 336 |
| Glu | Thr | Gly | Lys | Arg | Pro | Thr | Ala | Gly | Leu | Asp | Arg | Asn | Leu | Ala | Tyr | |
| | | | 100 | | | | | 105 | | | | | 110 | | | |
| ctc | ggc | ctc | gtg | gaa | gtg | ctt | tat | ggc | tat | ccg | ctc | gac | ggc | gtt | gtt | 384 |
| Leu | Gly | Leu | Val | Glu | Val | Leu | Tyr | Gly | Tyr | Pro | Leu | Asp | Gly | Val | Val | |
| | | 115 | | | | | 120 | | | | | 125 | | | | |
| ctg | acc | atc | ggc | tgc | gac | aag | acc | acg | cct | gcc | tgt | ctt | atg | gcg | gcg | 432 |
| Leu | Thr | Ile | Gly | Cys | Asp | Lys | Thr | Thr | Pro | Ala | Cys | Leu | Met | Ala | Ala | |
| | 130 | | | | | 135 | | | | | 140 | | | | | |
| gcc | acc | gtc | aac | att | ccg | gcc | atc | gcc | ctt | tcc | gtc | ggt | ccc | atg | ctg | 480 |
| Ala | Thr | Val | Asn | Ile | Pro | Ala | Ile | Ala | Leu | Ser | Val | Gly | Pro | Met | Leu | |
| 145 | | | | | 150 | | | | | 155 | | | | | 160 | |
| aac | ggc | tgg | ttc | cgc | ggt | gag | cgc | acc | ggt | tcc | ggc | acc | atc | gtc | tgg | 528 |
| Asn | Gly | Trp | Phe | Arg | Gly | Glu | Arg | Thr | Gly | Ser | Gly | Thr | Ile | Val | Trp | |
| | | | | 165 | | | | | 170 | | | | | 175 | | |
| aag | gcc | cgc | gaa | ctg | ctg | gcg | aag | ggc | gag | atc | gat | tac | cag | ggc | ttc | 576 |
| Lys | Ala | Arg | Glu | Leu | Leu | Ala | Lys | Gly | Glu | Ile | Asp | Tyr | Gln | Gly | Phe | |
| | | | 180 | | | | | 185 | | | | | 190 | | | |
| gtc | aag | ctc | gtt | gcc | tcg | tct | gcc | ccg | tcc | acc | ggc | tat | tgc | aac | acc | 624 |
| Val | Lys | Leu | Val | Ala | Ser | Ser | Ala | Pro | Ser | Thr | Gly | Tyr | Cys | Asn | Thr | |
| | | 195 | | | | | 200 | | | | | 205 | | | | |
| atg | ggc | acg | gca | aca | acc | atg | aac | tcg | ctc | gcc | gaa | gcg | ctc | ggc | atg | 672 |
| Met | Gly | Thr | Ala | Thr | Thr | Met | Asn | Ser | Leu | Ala | Glu | Ala | Leu | Gly | Met | |
| | 210 | | | | | 215 | | | | | 220 | | | | | |
| cag | ctt | ccc | ggc | tcc | gcc | gcc | att | ccg | gcg | cct | tac | cgt | gac | cgt | cag | 720 |
| Gln | Leu | Pro | Gly | Ser | Ala | Ala | Ile | Pro | Ala | Pro | Tyr | Arg | Asp | Arg | Gln | |
| 225 | | | | | 230 | | | | | 235 | | | | | 240 | |
| gaa | gtc | tct | tac | ctc | acc | ggc | ctg | cgc | atc | gtc | gac | atg | gtc | agg | gaa | 768 |
| Glu | Val | Ser | Tyr | Leu | Thr | Gly | Leu | Arg | Ile | Val | Asp | Met | Val | Arg | Glu | |
| | | | | 245 | | | | | 250 | | | | | 255 | | |

```
gac ctg aaa cca tca gac atc atg acc aag gat gcc ttc atc aac gcc    816
Asp Leu Lys Pro Ser Asp Ile Met Thr Lys Asp Ala Phe Ile Asn Ala
        260                 265                 270 atc cgc gtt aat tcg gcg atc ggc ggt tcc acc aac gcg ccg atc cat    864
Ile Arg Val Asn Ser Ala Ile Gly Gly Ser Thr Asn Ala Pro Ile His
            275                 280                 285 cta aac ggc ctt gcc cgc cat gtc ggc gtc gag ctg acg gtg gat gac    912
Leu Asn Gly Leu Ala Arg His Val Gly Val Glu Leu Thr Val Asp Asp
        290                 295                 300 tgg cag acc tat ggc gaa gac gtg ccg ctg ctc gtc aac ctg cag ccg    960
Trp Gln Thr Tyr Gly Glu Asp Val Pro Leu Leu Val Asn Leu Gln Pro
305                 310                 315                 320 gca ggc gaa tat ctc ggc gag gac tat tac cat gcc ggc ggc gtt ccc   1008
Ala Gly Glu Tyr Leu Gly Glu Asp Tyr Tyr His Ala Gly Gly Val Pro
                325                 330                 335 gct gtc gtc aat cag ctg atg acc caa ggg ctg atc atg gaa gac gcc   1056
Ala Val Val Asn Gln Leu Met Thr Gln Gly Leu Ile Met Glu Asp Ala
            340                 345                 350 atg acc gtc aac ggc aag acc atc ggc gac aat tgc cgt ggc gcg atc   1104
Met Thr Val Asn Gly Lys Thr Ile Gly Asp Asn Cys Arg Gly Ala Ile
        355                 360                 365 atc gaa gac gag aag gtc atc cgc ccc tat gag cag ccg ctc aag gag   1152
Ile Glu Asp Glu Lys Val Ile Arg Pro Tyr Glu Gln Pro Leu Lys Glu
    370                 375                 380 cgt gcc ggc ttc cgc gtt ctg cgc ggc aat ctg ttc tcc tcg gcc atc   1200
Arg Ala Gly Phe Arg Val Leu Arg Gly Asn Leu Phe Ser Ser Ala Ile
385                 390                 395                 400 atg aag aca agc gtg att tcg gaa gaa ttc cgc ggt cgt tac ctc tcc   1248
Met Lys Thr Ser Val Ile Ser Glu Glu Phe Arg Gly Arg Tyr Leu Ser
                405                 410                 415 aac cct gat gat ccg gaa gcc ttc gaa ggc cgc gcc gtg gtg ttc gat   1296
Asn Pro Asp Asp Pro Glu Ala Phe Glu Gly Arg Ala Val Val Phe Asp
            420                 425                 430 ggt ccg gag gat tac cat cat cgc atc gac gat ccg tcg ctt ggc atc   1344
Gly Pro Glu Asp Tyr His His Arg Ile Asp Asp Pro Ser Leu Gly Ile
        435                 440                 445 gac gcc aac acc gtc ctg ttc atg cgc ggc gcc ggt ccg atc ggt tac   1392
Asp Ala Asn Thr Val Leu Phe Met Arg Gly Ala Gly Pro Ile Gly Tyr
    450                 455                 460 ccg ggc gca gcg gaa gtg gtg aac atg cgc gcg ccg gat tac ctt ctg   1440
Pro Gly Ala Ala Glu Val Val Asn Met Arg Ala Pro Asp Tyr Leu Leu
465                 470                 475                 480 aag caa ggc gtc agt tcg ctg ccc tgc atc ggc gat ggc cgc cag tcc   1488
Lys Gln Gly Val Ser Ser Leu Pro Cys Ile Gly Asp Gly Arg Gln Ser
                485                 490                 495 ggc acg tcg ggc agc cca tcc atc ctc aat gcc tcg ccg gaa gcg gcg   1536
Gly Thr Ser Gly Ser Pro Ser Ile Leu Asn Ala Ser Pro Glu Ala Ala
            500                 505                 510 gcc ggc ggc ggt ctg tct att ctg cag acg ggt gac cgc gtc cgc atc   1584
Ala Gly Gly Gly Leu Ser Ile Leu Gln Thr Gly Asp Arg Val Arg Ile
        515                 520                 525 gat gtg ggc cgc ggc aag gcc gat atc ctg ata tca ggt gaa gag ctc   1632
Asp Val Gly Arg Gly Lys Ala Asp Ile Leu Ile Ser Gly Glu Glu Leu
    530                 535                 540 gcc aag cgt tac gag gcg ctg gca gct cag ggc ggt tat aag ttc ccc   1680
Ala Lys Arg Tyr Glu Ala Leu Ala Ala Gln Gly Gly Tyr Lys Phe Pro
545                 550                 555                 560 gac cac cag acg ccg tgg cag gaa atc cag cgc ggt atc gtc agc cag   1728
Asp His Gln Thr Pro Trp Gln Glu Ile Gln Arg Gly Ile Val Ser Gln
```

```
                565                 570                 575
atg gaa acc ggc gcg gtt ctg gaa ccg gcc gta aag tat cag cgc atc      1776
Met Glu Thr Gly Ala Val Leu Glu Pro Ala Val Lys Tyr Gln Arg Ile
            580                 585                 590 gcc cag acc aag ggc ctg ccg cgc gat aac cac tga                      1812
Ala Gln Thr Lys Gly Leu Pro Arg Asp Asn His
        595                 600

<210> SEQ ID NO 2
<211> LENGTH: 603
<212> TYPE: PRT
<213> ORGANISM: Agrobacterium tumefaciens

<400> SEQUENCE: 2

Met Thr Thr Ser Asp Asn Leu Pro Ala Thr Gln Gly Lys Leu Arg Ser
1               5                   10                  15

Arg Ala Trp Phe Asp Asn Pro Ala Asn Ala Asp Met Thr Ala Leu Tyr
            20                  25                  30

Leu Glu Arg Tyr Met Asn Phe Gly Leu Ser Gln Ala Glu Leu Gln Ser
        35                  40                  45

Asp Arg Pro Ile Ile Gly Ile Ala Gln Thr Gly Ser Asp Leu Ser Pro
    50                  55                  60

Cys Asn Arg His His Leu Glu Leu Ala Asn Arg Leu Arg Glu Gly Ile
65                  70                  75                  80

Arg Glu Ala Gly Gly Ile Ala Ile Glu Phe Pro Val His Pro Ile Gln
                85                  90                  95

Glu Thr Gly Lys Arg Pro Thr Ala Gly Leu Asp Arg Asn Leu Ala Tyr
            100                 105                 110

Leu Gly Leu Val Glu Val Leu Tyr Gly Tyr Pro Leu Asp Gly Val Val
        115                 120                 125

Leu Thr Ile Gly Cys Asp Lys Thr Thr Pro Ala Cys Leu Met Ala Ala
    130                 135                 140

Ala Thr Val Asn Ile Pro Ala Ile Ala Leu Ser Val Gly Pro Met Leu
145                 150                 155                 160

Asn Gly Trp Phe Arg Gly Glu Arg Thr Gly Ser Gly Thr Ile Val Trp
                165                 170                 175

Lys Ala Arg Glu Leu Leu Ala Lys Gly Glu Ile Asp Tyr Gln Gly Phe
            180                 185                 190

Val Lys Leu Val Ala Ser Ser Ala Pro Ser Thr Gly Tyr Cys Asn Thr
        195                 200                 205

Met Gly Thr Ala Thr Thr Met Asn Ser Leu Ala Glu Ala Leu Gly Met
    210                 215                 220

Gln Leu Pro Gly Ser Ala Ala Ile Pro Ala Pro Tyr Arg Asp Arg Gln
225                 230                 235                 240

Glu Val Ser Tyr Leu Thr Gly Leu Arg Ile Val Asp Met Val Arg Glu
                245                 250                 255

Asp Leu Lys Pro Ser Asp Ile Met Thr Lys Asp Ala Phe Ile Asn Ala
            260                 265                 270

Ile Arg Val Asn Ser Ala Ile Gly Gly Ser Thr Asn Ala Pro Ile His
        275                 280                 285

Leu Asn Gly Leu Ala Arg His Val Gly Val Glu Leu Thr Val Asp Asp
    290                 295                 300

Trp Gln Thr Tyr Gly Glu Asp Val Pro Leu Leu Val Asn Leu Gln Pro
305                 310                 315                 320

Ala Gly Glu Tyr Leu Gly Glu Asp Tyr Tyr His Ala Gly Gly Val Pro
```

-continued

```
               325                 330                 335
Ala Val Val Asn Gln Leu Met Thr Gln Gly Leu Ile Met Glu Asp Ala
            340                 345                 350

Met Thr Val Asn Gly Lys Thr Ile Gly Asp Asn Cys Arg Gly Ala Ile
        355                 360                 365

Ile Glu Asp Glu Lys Val Ile Arg Pro Tyr Glu Gln Pro Leu Lys Glu
    370                 375                 380

Arg Ala Gly Phe Arg Val Leu Arg Gly Asn Leu Phe Ser Ser Ala Ile
385                 390                 395                 400

Met Lys Thr Ser Val Ile Ser Glu Glu Phe Arg Gly Arg Tyr Leu Ser
                405                 410                 415

Asn Pro Asp Asp Pro Glu Ala Phe Glu Gly Arg Ala Val Val Phe Asp
            420                 425                 430

Gly Pro Glu Asp Tyr His His Arg Ile Asp Asp Pro Ser Leu Gly Ile
        435                 440                 445

Asp Ala Asn Thr Val Leu Phe Met Arg Gly Ala Gly Pro Ile Gly Tyr
    450                 455                 460

Pro Gly Ala Ala Glu Val Val Asn Met Arg Ala Pro Asp Tyr Leu Leu
465                 470                 475                 480

Lys Gln Gly Val Ser Ser Leu Pro Cys Ile Gly Asp Gly Arg Gln Ser
                485                 490                 495

Gly Thr Ser Gly Ser Pro Ser Ile Leu Asn Ala Ser Pro Glu Ala Ala
            500                 505                 510

Ala Gly Gly Gly Leu Ser Ile Leu Gln Thr Gly Asp Arg Val Arg Ile
        515                 520                 525

Asp Val Gly Arg Gly Lys Ala Asp Ile Leu Ile Ser Gly Glu Glu Leu
    530                 535                 540

Ala Lys Arg Tyr Glu Ala Leu Ala Ala Gln Gly Gly Tyr Lys Phe Pro
545                 550                 555                 560

Asp His Gln Thr Pro Trp Gln Glu Ile Gln Arg Gly Ile Val Ser Gln
                565                 570                 575

Met Glu Thr Gly Ala Val Leu Glu Pro Ala Val Lys Tyr Gln Arg Ile
            580                 585                 590

Ala Gln Thr Lys Gly Leu Pro Arg Asp Asn His
        595                 600
```

<210> SEQ ID NO 3
<211> LENGTH: 1272
<212> TYPE: DNA
<213> ORGANISM: Agrobacterium tumefaciens
<220> FEATURE:
<221> NAME/KEY: CDS
<222> LOCATION: (1)..(1269)
<223> OTHER INFORMATION:

<400> SEQUENCE: 3

```
atg cag tct tct tca gct ctt cgg caa tca acc ggc gat cag tcg gaa    48
Met Gln Ser Ser Ser Ala Leu Arg Gln Ser Thr Gly Asp Gln Ser Glu
1               5                   10                  15 tac cat gcc cag tcg aat atg atc ggc tct agc ccg gcg gac ggt ttg    96
Tyr His Ala Gln Ser Asn Met Ile Gly Ser Ser Pro Ala Asp Gly Leu
            20                  25                  30 ctc gca ttg ccg ctt ctg acc gtc gat ctt gcc gtc tat cgc ggt aat    144
Leu Ala Leu Pro Leu Leu Thr Val Asp Leu Ala Val Tyr Arg Gly Asn
        35                  40                  45 cgg gat cgc ttt ctt gcg ctt gtc tcg gcc cat gga gcg aag gcg gct    192
Arg Asp Arg Phe Leu Ala Leu Val Ser Ala His Gly Ala Lys Ala Ala
    50                  55                  60
```

-continued

```
              50                  55                  60
cca cat gcc aag acg ccg atg tgc ccg gag atc gcg atc gat ctg att     240
Pro His Ala Lys Thr Pro Met Cys Pro Glu Ile Ala Ile Asp Leu Ile
 65              70                  75                  80 gaa gcc ggt gcc tgg ggc gcg acg gtc gcc gat ctc ttc cag gcg aa     288
Glu Ala Gly Ala Trp Gly Ala Thr Val Ala Asp Leu Phe Gln Ala Glu
                 85                  90                  95 gtc ctg ctc aag gcc ggc gtg tcg aac ata ttg atc gcc aac cag atc     336
Val Leu Leu Lys Ala Gly Val Ser Asn Ile Leu Ile Ala Asn Gln Ile
            100                 105                 110 ggc gga ttg aca tcc gcc aga cgc cta cgc atg ctc gca gat gct ttt     384
Gly Gly Leu Thr Ser Ala Arg Arg Leu Arg Met Leu Ala Asp Ala Phe
            115                 120                 125 ccg aaa gcc gag att atc tgc tgt gtc gat tct gtt cag gcc tcg gcc     432
Pro Lys Ala Glu Ile Ile Cys Cys Val Asp Ser Val Gln Ala Ser Ala
130                 135                 140 aat ctg gtt cag gcc ttt caa ggg cgt gtg gat gcc cca ttc aag gtc     480
Asn Leu Val Gln Ala Phe Gln Gly Arg Val Asp Ala Pro Phe Lys Val
145                 150                 155                 160 ttc atc gaa gtc ggt gtc ggc cgc act ggc gcc cgt acg ttg aat gtt     528
Phe Ile Glu Val Gly Val Gly Arg Thr Gly Ala Arg Thr Leu Asn Val
                165                 170                 175 gca aag gat atc atc gac acc atc tcg aca agt gca gaa atc gta ctg     576
Ala Lys Asp Ile Ile Asp Thr Ile Ser Thr Ser Ala Glu Ile Val Leu
            180                 185                 190 gcc ggt gtg tcg acc tat gaa ggc tcc gtc tcc ggg gaa acg tcg gaa     624
Ala Gly Val Ser Thr Tyr Glu Gly Ser Val Ser Gly Glu Thr Ser Glu
            195                 200                 205 gca ctc gat gca aac atg gcg gcc ctg ttc gat ctc ctg acc gac agt     672
Ala Leu Asp Ala Asn Met Ala Ala Leu Phe Asp Leu Leu Thr Asp Ser
210                 215                 220 ctt gca tcg ata cgc gaa aaa gat ccc ggg cgc ccg cta acg gtt tca     720
Leu Ala Ser Ile Arg Glu Lys Asp Pro Gly Arg Pro Leu Thr Val Ser
225                 230                 235                 240 gcc ggc ggt tcg atc cat ttc gac cgc gtg ctc gcg gcg ctt gtg ccc     768
Ala Gly Gly Ser Ile His Phe Asp Arg Val Leu Ala Ala Leu Val Pro
                245                 250                 255 gtt tgc gag gcg gat ggc aat gcg acg ttg ttg ctg cgc agc ggc gcc     816
Val Cys Glu Ala Asp Gly Asn Ala Thr Leu Leu Leu Arg Ser Gly Ala
                260                 265                 270 atc ttc ttc tct gat cac ggt gta tat cag cgc ggt ttc cag gca gtc     864
Ile Phe Phe Ser Asp His Gly Val Tyr Gln Arg Gly Phe Gln Ala Val
            275                 280                 285 gac gcc cgc aac cta ctc gca tcc ggc aag gtt gtc ttc aag gca tcc     912
Asp Ala Arg Asn Leu Leu Ala Ser Gly Lys Val Val Phe Lys Ala Ser
290                 295                 300 gag gca ttt cag ccc tca atg cga atc tgg gcg gag gtc atc tcc gtt     960
Glu Ala Phe Gln Pro Ser Met Arg Ile Trp Ala Glu Val Ile Ser Val
305                 310                 315                 320 cct gag ccg ggg ctg gcg atc gtc ggc atg ggc atg cgg gat gta tcg    1008
Pro Glu Pro Gly Leu Ala Ile Val Gly Met Gly Met Arg Asp Val Ser
                325                 330                 335 ttc gat cag gac ctg ccc gtg gcg ctt cgg ctc cat agg gac gga cat    1056
Phe Asp Gln Asp Leu Pro Val Ala Leu Arg Leu His Arg Asp Gly His
                340                 345                 350 ctg gtc gaa gct gat ctc tct tca tcc gcg aag gtc ggc aag ctc aat    1104
Leu Val Glu Ala Asp Leu Ser Ser Ser Ala Lys Val Gly Lys Leu Asn
            355                 360                 365 gac cag cat gcc ttc ttg tcc ttc ggg aac ggc agc agt ctg gca atc    1152
Asp Gln His Ala Phe Leu Ser Phe Gly Asn Gly Ser Ser Leu Ala Ile
```

-continued

```
Asp Gln His Ala Phe Leu Ser Phe Gly Asn Gly Ser Ser Leu Ala Ile
    370                 375                 380 ggc gat gtc ata gaa ttc ggc atc tcg cat ccc tgc acg tgc ttc gat      1200
Gly Asp Val Ile Glu Phe Gly Ile Ser His Pro Cys Thr Cys Phe Asp
385                 390                 395                 400 cgc tgg cgc gtc ttt cac gga atc gat gga tca ggc gg atc cag cgc       1248
Arg Trp Arg Val Phe His Gly Ile Asp Gly Ser Gly Arg Ile Gln Arg
                405                 410                 415 atc tac aca acc ttc ttt cac tag                                      1272
Ile Tyr Thr Thr Phe Phe His
                420
```

<210> SEQ ID NO 4
<211> LENGTH: 423
<212> TYPE: PRT
<213> ORGANISM: Agrobacterium tumefaciens

<400> SEQUENCE: 4

```
Met Gln Ser Ser Ser Ala Leu Arg Gln Ser Thr Gly Asp Gln Ser Glu
1               5                   10                  15

Tyr His Ala Gln Ser Asn Met Ile Gly Ser Ser Pro Ala Asp Gly Leu
                20                  25                  30

Leu Ala Leu Pro Leu Leu Thr Val Asp Leu Ala Val Tyr Arg Gly Asn
            35                  40                  45

Arg Asp Arg Phe Leu Ala Leu Val Ser Ala His Gly Ala Lys Ala Ala
        50                  55                  60

Pro His Ala Lys Thr Pro Met Cys Pro Glu Ile Ala Ile Asp Leu Ile
65                  70                  75                  80

Glu Ala Gly Ala Trp Gly Ala Thr Val Ala Asp Leu Phe Gln Ala Glu
                85                  90                  95

Val Leu Leu Lys Ala Gly Val Ser Asn Ile Leu Ile Ala Asn Gln Ile
            100                 105                 110

Gly Gly Leu Thr Ser Ala Arg Arg Leu Arg Met Leu Ala Asp Ala Phe
        115                 120                 125

Pro Lys Ala Glu Ile Ile Cys Cys Val Asp Ser Val Gln Ala Ser Ala
    130                 135                 140

Asn Leu Val Gln Ala Phe Gln Gly Arg Val Asp Ala Pro Phe Lys Val
145                 150                 155                 160

Phe Ile Glu Val Gly Val Gly Arg Thr Gly Ala Arg Thr Leu Asn Val
                165                 170                 175

Ala Lys Asp Ile Ile Asp Thr Ile Ser Thr Ser Ala Glu Ile Val Leu
            180                 185                 190

Ala Gly Val Ser Thr Tyr Glu Gly Ser Val Ser Gly Glu Thr Ser Glu
        195                 200                 205

Ala Leu Asp Ala Asn Met Ala Ala Leu Phe Asp Leu Leu Thr Asp Ser
    210                 215                 220

Leu Ala Ser Ile Arg Glu Lys Asp Pro Gly Arg Pro Leu Thr Val Ser
225                 230                 235                 240

Ala Gly Gly Ser Ile His Phe Asp Arg Val Leu Ala Ala Leu Val Pro
                245                 250                 255

Val Cys Glu Ala Asp Gly Asn Ala Thr Leu Leu Leu Arg Ser Gly Ala
            260                 265                 270

Ile Phe Phe Ser Asp His Gly Val Tyr Gln Arg Gly Phe Gln Ala Val
        275                 280                 285

Asp Ala Arg Asn Leu Leu Ala Ser Gly Lys Val Val Phe Lys Ala Ser
    290                 295                 300
```

-continued

```
Glu Ala Phe Gln Pro Ser Met Arg Ile Trp Ala Glu Val Ile Ser Val
305                 310                 315                 320

Pro Glu Pro Gly Leu Ala Ile Val Gly Met Gly Met Arg Asp Val Ser
            325                 330                 335

Phe Asp Gln Asp Leu Pro Val Ala Leu Arg Leu His Arg Asp Gly His
        340                 345                 350

Leu Val Glu Ala Asp Leu Ser Ser Ser Ala Lys Val Gly Lys Leu Asn
    355                 360                 365

Asp Gln His Ala Phe Leu Ser Phe Gly Asn Gly Ser Ser Leu Ala Ile
    370                 375                 380

Gly Asp Val Ile Glu Phe Gly Ile Ser His Pro Cys Thr Cys Phe Asp
385                 390                 395                 400

Arg Trp Arg Val Phe His Gly Ile Asp Gly Ser Gly Arg Ile Gln Arg
                405                 410                 415

Ile Tyr Thr Thr Phe Phe His
            420

<210> SEQ ID NO 5
<211> LENGTH: 32
<212> TYPE: DNA
<213> ORGANISM: artificial sequence
<220> FEATURE:
<223> OTHER INFORMATION: oligonucleotide primer

<400> SEQUENCE: 5
cccttaatta atgacgacat ctgataatct tc                              32

<210> SEQ ID NO 6
<211> LENGTH: 30
<212> TYPE: DNA
<213> ORGANISM: artificial sequence
<220> FEATURE:
<223> OTHER INFORMATION: oligonucleotide primer

<400> SEQUENCE: 6
tttgcggccg cttagtggtt atcgcgcggc                                 30

<210> SEQ ID NO 7
<211> LENGTH: 31
<212> TYPE: DNA
<213> ORGANISM: artificial sequence
<220> FEATURE:
<223> OTHER INFORMATION: oligonucleotide primer

<400> SEQUENCE: 7
cccggtacca tgacgacatc tgataatctt c                               31

<210> SEQ ID NO 8
<211> LENGTH: 32
<212> TYPE: DNA
<213> ORGANISM: artificial sequence
<220> FEATURE:
<223> OTHER INFORMATION: oligonucleotide primer

<400> SEQUENCE: 8
cccttaatta atgcagtctt cttcagctct tc                              32

<210> SEQ ID NO 9
<211> LENGTH: 35
<212> TYPE: DNA
<213> ORGANISM: artificial sequence
<220> FEATURE:
```

-continued

```
<223> OTHER INFORMATION: oligonucleotide primer

<400> SEQUENCE: 9
tttgcggccg cctagtgaaa gaaggttgtg tagat                              35

<210> SEQ ID NO 10
<211> LENGTH: 34
<212> TYPE: DNA
<213> ORGANISM: artificial sequence
<220> FEATURE:
<223> OTHER INFORMATION: oligonucleotide primer

<400> SEQUENCE: 10
aaatcatgac tatgcagtct tcttcagctc ttcg                              34

<210> SEQ ID NO 11
<211> LENGTH: 33
<212> TYPE: DNA
<213> ORGANISM: artificial sequence
<220> FEATURE:
<223> OTHER INFORMATION: oligonucleotide primer

<400> SEQUENCE: 11
tatagatctc tagtgaaaga aggttgtgta gat                               33

<210> SEQ ID NO 12
<211> LENGTH: 31
<212> TYPE: DNA
<213> ORGANISM: artificial sequence
<220> FEATURE:
<223> OTHER INFORMATION: artificial sequence

<400> SEQUENCE: 12
gcgttaatta atgagttata ctgtcggtac c                                 31

<210> SEQ ID NO 13
<211> LENGTH: 32
<212> TYPE: DNA
<213> ORGANISM: artificial sequence
<220> FEATURE:
<223> OTHER INFORMATION: artificial sequence

<400> SEQUENCE: 13
tatgcggccg cttagaggag cttgttaaca gg                                32

<210> SEQ ID NO 14
<211> LENGTH: 2665
<212> TYPE: DNA
<213> ORGANISM: vector

<400> SEQUENCE: 14
gacgaaaggg cctcgtgata cgcctatttt tataggttaa tgtcatgata ataatggttt    60
cttagacgtc aggtggcact tttcggggaa atgtgcgcgg aacccctatt tgtttatttt   120
tctaaataca ttcaaatatg tatccgctca tgagacaata accctgataa atgcttcaat   180
aatattgaaa aaggaagagt atgagtattc aacatttccg tgtcgccctt attccctttt   240
ttgcggcatt ttgccttcct gtttttgctc acccagaaac gctggtgaaa gtaaaagatg   300
ctgaagatca gttgggtgca cgagtgggtt acatcgaact ggatctcaac agcggtaaga   360
tccttgagag ttttcgcccc gaagaacgtt ttccaatgat gagcactttt aaagttctgc   420
tatgtggcgc ggtattatcc cgtattgacg ccgggcaaga gcaactcggt cgccgcatac   480
actattctca gaatgacttg gttgagtact caccagtcac agaaaagcat cttacggatg   540
```

```
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tccttttga taatctcatg accaaaatcc cttaacgtga gttttcgttc cactgagcgt   1200
cagaccccgt agaaaagatc aaaggatctt cttgagatcc ttttttttctg cgcgtaatct   1260
gctgcttgca acaaaaaaac caccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga cggggggtt   1560
cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
ggggggcggag cctatggaaa aacgccagca acgcggcctt tttacggttc ctggcctttt   1860
gctggccttt tgctcacatg ttcttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcaccccca ggctttacac tttatgcttc   2160
cggctcgtat gttgtgtgga attgtgagcg gataacaatt tcacacagga aacagctatg   2220
accatgatta cgaattcgag gttaattaac cccgcggccg caagcttggc actggccgtc   2280
gttttacaac gtcgtgactg ggaaaaccct ggcgttaccc aacttaatcg ccttgcagca   2340
catcccccctt tcgccagctg gcgtaatagc gaagaggccc gcaccgatcg cccttcccaa   2400
cagttgcgca gcctgaatgg cgaatggcgc ctgatgcggt attttctcct tacgcatctg   2460
tgcggtattt cacaccgcat atggtgcact ctcagtacaa tctgctctga tgccgcatag   2520
ttaagccagc cccgacaccc gccaacaccc gctgacgcgc cctgacgggc ttgtctgctc   2580
ccggcatccg cttacagaca agctgtgacc gtctccggga gctgcatgtg tcagaggttt   2640
tcaccgtcat caccgaaacg cgcga                                         2665

<210> SEQ ID NO 15
<211> LENGTH: 3433
<212> TYPE: DNA
<213> ORGANISM: vector
```

```
<400> SEQUENCE: 15
ctcgagaaat cataaaaaat ttatttgctt tgtgagcgga taacaattat aatagattca      60
attgtgagcg gataacaatt tcacacagaa ttcttaaaga ggagaaatta attaccccg      120
cggccgcgga tccagatctc atcaccatca ccatcactaa gcttaattag ctgagcttgg     180
actcctgttg atagatccag taatgacctc agaactccat ctggatttgt tcagaacgct     240
cggttgccgc cgggcgtttt ttattggtga gaatccaagc tagcttggcg agattttcag     300
gagctaagga agctaaaatg gagaaaaaaa tcactggata taccaccgtt gatatatccc     360
aatggcatcg taaagaacat tttgaggcat ttcagtcagt tgctcaatgt acctataacc     420
agaccgttca gctggatatt acggcctttt taaagaccgt aaagaaaaat aagcacaagt     480
tttatccggc ctttattcac attcttgccc gcctgatgaa tgctcatccg gaatttcgta     540
tggcaatgaa agacggtgag ctggtgatat gggatagtgt tcacccttgt tacaccgttt     600
tccatgagca aactgaaacg ttttcatcgc tctggagtga ataccacgac gatttccggc     660
agtttctaca catatattcg caagatgtgg cgtgttacgg tgaaaacctg gcctatttcc     720
ctaaagggtt tattgagaat atgttttttcg tctcagccaa tccctgggtg agtttcacca     780
gttttgattt aaacgtggcc aatatggaca acttcttcgc ccccgttttc accatgggca     840
aatattatac gcaaggcgac aaggtgctga tgccgctggc gattcaggtt catcatgccg     900
tttgtgatgg cttccatgtc ggcagaatgc ttaatgaatt acaacagtac tgcgatgagt     960
ggcagggcgg ggcgtaattt ttttaaggca gttattggtg cccttaaacg cctggggtaa    1020
tgactctcta gcttgaggca tcaaataaaa cgaaaggctc agtcgaaaga ctgggccttt    1080
cgttttatct gttgtttgtc ggtgaacgct ctcctgagta ggacaaatcc gccctctaga    1140
gctgcctcgc gcgtttcggt gatgacgtg aaaacctctg acacatgcag ctcccggaga    1200
cggtcacagc ttgtctgtaa gcggatgccg ggagcagaca gcccgtcag ggcgcgtcag    1260
cgggtgttgg cgggtgtcgg ggcgcagcca tgacccagtc acgtagcgat agcggagtgt    1320
atactggctt aactatgcgg catcagagca gattgtactg agagtgcacc atatgcggtg    1380
tgaaataccg cacagatgcg taaggagaaa ataccgcatc aggcgctctt ccgcttcctc    1440
gctcactgac tcgctgcgct cggtcgttcg gctgcggcga gcggtatcag ctcactcaaa    1500
ggcggtaata cggttatcca cagaatcagg ggataacgca ggaaagaaca tgtgagcaaa    1560
aggccagcaa aaggccagga accgtaaaaa ggccgcgttg ctggcgtttt tccataggct    1620
ccgcccccct gacgagcatc acaaaaatcg acgctcaagt cagaggtggc gaaacccgac    1680
aggactataa agataccagg cgtttccccc tggaagctcc ctcgtgcgct ctcctgttcc    1740
gaccctgccg cttaccggat acctgtccgc ctttctccct tcgggaagcg tggcgctttc    1800
tcatagctca cgctgtaggt atctcagttc ggtgtaggtc gttcgctcca agctgggctg    1860
tgtgcacgaa ccccccgttc agcccgaccg ctgcgcctta tccggtaact atcgtcttga    1920
gtccaacccg gtaagacacg acttatcgcc actggcagca gccactggta acaggattag    1980
cagagcgagg tatgtaggcg gtgctacaga gttcttgaag tggtggccta actacggcta    2040
cactagaagg acagtatttg gtatctgcgc tctgctgaag ccagttacct tcggaaaaag    2100
agttggtagc tcttgatccg gcaaacaaac caccgctggt agcggtggtt tttttgtttg    2160
caagcagcag attacgcgca gaaaaaaagg atctcaagaa gatcctttga tcttttctac    2220
ggggtctgac gctcagtgga acgaaaactc acgttaaggg attttggtca tgagattatc    2280
aaaaaggatc ttcacctaga tccttttaaa ttaaaaatga agttttaaat caatctaaag    2340
```

```
tatatatgag taaacttggt ctgacagtta ccaatgctta atcagtgagg cacctatctc    2400
agcgatctgt ctatttcgtt catccatagt tgcctgactc cccgtcgtgt agataactac    2460
gatacgggag ggcttaccat ctggccccag tgctgcaatg ataccgcgag acccacgctc    2520
accggctcca gatttatcag caataaacca gccagccgga agggccgagc gcagaagtgg    2580
tcctgcaact ttatccgcct ccatccagtc tattaattgt tgccgggaag ctagagtaag    2640
tagttcgcca gttaatagtt tgcgcaacgt tgttgccatt gctacaggca tcgtggtgtc    2700
acgctcgtcg tttggtatgg cttcattcag ctccggttcc caacgatcaa ggcgagttac    2760
atgatccccc atgttgtgca aaaaagcggt tagctccttc ggtcctccga tcgttgtcag    2820
aagtaagttg gccgcagtgt tatcactcat ggttatggca gcactgcata attctcttac    2880
tgtcatgcca tccgtaagat gcttttctgt gactggtgag tactcaacca agtcattctg    2940
agaatagtgt atgcggcgac cgagttgctc ttgcccggcg tcaatacggg ataataccgc    3000
gccacatagc agaactttaa aagtgctcat cattggaaaa cgttcttcgg ggcgaaaact    3060
ctcaaggatc ttaccgctgt tgagatccag ttcgatgtaa cccactcgtg cacccaactg    3120
atcttcagca tcttttactt tcaccagcgt ttctgggtga gcaaaaacag gaaggcaaaa    3180
tgccgcaaaa aagggaataa gggcgacacg gaaatgttga atactcatac tcttcctttt    3240
tcaatattat tgaagcattt atcagggtta ttgtctcatg agcggataca tatttgaatg    3300
tatttagaaa aataaacaaa taggggttcc gcgcacattt ccccgaaaag tgccacctga    3360
cgtctaagaa accattatta tcatgacatt aacctataaa aataggcgta tcacgaggcc    3420
ctttcgtctt cac                                                      3433

<210> SEQ ID NO 16
<211> LENGTH: 30
<212> TYPE: DNA
<213> ORGANISM: artificial sequence
<220> FEATURE:
<223> OTHER INFORMATION: artificial sequence

<400> SEQUENCE: 16
atatttaatt aatgtctgaa attactttgg                                       30

<210> SEQ ID NO 17
<211> LENGTH: 30
<212> TYPE: DNA
<213> ORGANISM: artificial sequence
<220> FEATURE:
<223> OTHER INFORMATION: artificial sequence

<400> SEQUENCE: 17
atatgcggcc gcttattgct tagcgttggt                                       30
```